(12) United States Patent
Meghpara et al.

(10) Patent No.: US 12,042,559 B2
(45) Date of Patent: *Jul. 23, 2024

(54) GASTRORETENTIVE DOSAGE FORMS FOR SUSTAINED DRUG DELIVERY

(71) Applicant: AMNEAL COMPLEX PRODUCTS RESEARCH LLC, Bridgewater, NJ (US)

(72) Inventors: Kanji Meghpara, Morris Plains, NJ (US); Jaydeep Vagashiya, Franklin Park, NJ (US); Navnit H. Shah, Monmouth Junction, NJ (US); Dipen Desai, Basking Ridge, NJ (US); Wantanee Phuapradit, Lewes, DE (US); Harpreet Kaur Sandhu, West Orange, NJ (US); Siva Ram Kiran Vaka, Piscataway, NJ (US); Namdev B. Shelke, Hillsborough, NJ (US); Ashish Chatterji, East Brunswick, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/231,449

(22) Filed: Aug. 8, 2023

(65) Prior Publication Data

US 2023/0404916 A1 Dec. 21, 2023

Related U.S. Application Data

(63) Continuation of application No. 17/703,102, filed on Mar. 24, 2022, which is a continuation of application No. 17/233,873, filed on Apr. 19, 2021, now Pat. No. 11,318,091, which is a continuation of application No. 17/064,949, filed on Oct. 7, 2020, now Pat. No. 11,007,145, which is a continuation of application No. 16/868,056, filed on May 6, 2020, now Pat. No. 10,857,098, which is a continuation of application No. 16/319,086, filed as application No. PCT/US2018/038118 on Jun. 18, 2018, now Pat. No. 10,918,597.

(60) Provisional application No. 62/520,796, filed on Jun. 16, 2017.

(51) Int. Cl.
| | | |
|---|---|---|
| A61K 9/00 | (2006.01) |
| A61K 9/28 | (2006.01) |
| A61K 9/46 | (2006.01) |
| A61K 31/195 | (2006.01) |
| A61K 31/198 | (2006.01) |
| A61K 31/403 | (2006.01) |
| A61K 31/404 | (2006.01) |
| A61K 31/4166 | (2006.01) |
| A61K 31/421 | (2006.01) |
| A61K 31/4412 | (2006.01) |
| A61K 31/4425 | (2006.01) |
| A61K 47/32 | (2006.01) |
| A61K 47/34 | (2017.01) |
| A61K 47/38 | (2006.01) |

(52) U.S. Cl.
CPC .......... *A61K 9/0065* (2013.01); *A61K 9/0007* (2013.01); *A61K 9/284* (2013.01); *A61K 31/195* (2013.01); *A61K 31/198* (2013.01); *A61K 31/403* (2013.01); *A61K 31/404* (2013.01); *A61K 31/4166* (2013.01); *A61K 31/421* (2013.01); *A61K 31/4412* (2013.01); *A61K 31/4425* (2013.01); *A61K 47/32* (2013.01); *A61K 47/34* (2013.01); *A61K 47/38* (2013.01)

(58) Field of Classification Search
CPC .... A61K 9/0065; A61K 9/284; A61K 31/195; A61K 31/403; A61K 31/421; A61K 31/4412
See application file for complete search history.

(56) References Cited

U.S. PATENT DOCUMENTS

| | | | | |
|---|---|---|---|---|
| 4,101,650 A | * | 7/1978 | Umezawa | A61K 9/0065 424/490 |
| 4,777,033 A | * | 10/1988 | Ikura | A61K 9/2027 424/44 |
| 4,844,905 A | * | 7/1989 | Ichikawa | A61K 9/5078 424/451 |
| 6,340,475 B2 | * | 1/2002 | Shell | A61K 9/205 424/464 |

(Continued)

FOREIGN PATENT DOCUMENTS

| | | | | |
|---|---|---|---|---|
| CN | 102258496 B | * | 1/2013 | |
| CN | 105434403 A | * | 3/2016 | A61K 31/4425 |

(Continued)

OTHER PUBLICATIONS

Deshpande et al., "Development of a Novel Controlled-Release System for Gastric Retention," Pharmaceutical Research, 14(6):815-819 (Year: 1997).*

Deshpande et al., "Evaluation of films used in development of a novel controlled-release system for gastric retention," International Journal of Pharmaceutics, 159:255-258 (Year: 1997).*

Huang et al., "An investigation of acetylcholine released in skeletal muscle and protein unbound drug released in blood based on the pyridostigmine bromide (pretreatment drug) sustained-release pellets by microdialysis technique in the rabbit model," Neuroscience Letters 416:302-306 (Year: 2007).*

J. Goole, Deleuze, F. Vanderbist, and K. Amighi, "New levodopa sustained-release floating minitablets coated with insoluble acrylic polymer", European Journal of Pharmaceutics and Biopharmaceutics 68 (2008) 310-318 (Year: 2008).*

(Continued)

*Primary Examiner* — Mina Haghighatian
*Assistant Examiner* — Nathan W Schlientz

(57) ABSTRACT

The present disclosure is directed to floating gastroretentive dosage forms with prolonged gastric residence time. The disclosure also provides rapidly expanding sustained release or combined immediate release and sustained release formulations comprising drugs that require targeted release in the proximal gastrointestinal tract for maximum therapeutic benefit. The rapidly expanding floating gastroretentive dosage forms comprise a permeable elastic membrane providing desired characteristics for drug release and mechanical strength to maintain tablet integrity.

20 Claims, 20 Drawing Sheets

(56) References Cited

U.S. PATENT DOCUMENTS

| | | | | |
|---|---|---|---|---|
| 6,488,962 | B1* | 12/2002 | Berner | A61K 9/2072 424/464 |
| 6,531,153 | B2* | 3/2003 | Seth | A61K 9/2013 424/488 |
| 6,635,280 | B2* | 10/2003 | Shell | A61K 9/2054 424/464 |
| 6,682,759 | B2* | 1/2004 | Lim | A61K 31/155 424/479 |
| 6,723,340 | B2* | 4/2004 | Gusler | A61K 9/0065 424/468 |
| 7,094,427 | B2* | 8/2006 | Han | A61K 31/198 |
| 7,776,345 | B2* | 8/2010 | Dudhara | A61P 21/02 424/471 |
| 7,976,870 | B2* | 7/2011 | Berner | A61P 31/06 424/464 |
| 8,043,630 | B2* | 10/2011 | Berner | A61K 31/60 424/464 |
| 8,329,215 | B2* | 12/2012 | Berner et al. | A61K 31/4178 |
| 8,685,450 | B2* | 4/2014 | Lim et al. | A61K 31/421 |
| 8,999,388 | B2* | 4/2015 | Lim et al. | A61P 25/16 |
| 9,161,911 | B2* | 10/2015 | Hou | A61K 47/34 |
| 8,945,619 | B2* | 12/2015 | Berner et al. | A61K 9/1676 |
| 9,439,851 | B2* | 9/2016 | Dharmadhkari et al. A61K 9/0065 |
| 9,566,258 | B2* | 2/2017 | Hou | A61K 9/2846 |
| 9,572,780 | B2* | 2/2017 | Lim et al. | A61K 9/2846 |
| 9,597,338 | B2* | 3/2017 | Berner et al. | A61K 9/2846 |
| 9,937,142 | B2* | 4/2018 | Hou | A61K 31/198 |
| 9,980,903 | B2* | 5/2018 | Berner | A61P 21/04 |
| 10,588,863 | B2* | 3/2020 | Vaka | A61K 9/2866 |
| 10,744,083 | B2* | 8/2020 | Shah | A61K 31/4164 |
| 10,744,093 | B2* | 8/2020 | Vaka | A61K 9/2013 |
| 10,849,846 | B2* | 12/2020 | Shah | A61K 31/4178 |
| 10,857,098 | B2* | 12/2020 | Meghpara | A61K 31/421 |
| 10,881,617 | B1* | 1/2021 | Vaka | A61K 9/1676 |
| 10,898,430 | B2* | 1/2021 | Shah | A61P 25/16 |
| 10,918,597 | B2* | 2/2021 | Meghpara | A61K 47/34 |
| 10,925,833 | B2* | 2/2021 | Shelke | A61K 9/0065 |
| 10,952,957 | B2* | 3/2021 | Shah | A61K 9/2846 |
| 10,987,311 | B2* | 4/2021 | Vaka | A61K 9/2846 |
| 11,007,145 | B2* | 5/2021 | Meghpara | A61K 9/2846 |
| 11,179,320 | B2* | 11/2021 | Shah | A61K 31/198 |
| 11,229,606 | B2* | 1/2022 | Vaka | A61P 21/04 |
| 11,318,091 | B2* | 5/2022 | Meghpara | A61K 9/284 |
| 11,478,425 | B2* | 10/2022 | Shelke | A61K 9/2027 |
| 11,666,536 | B2* | 6/2023 | Vaka | A61K 9/5073 424/472 |
| 2002/0051820 | A1* | 5/2002 | Shell | A61K 9/2013 424/487 |
| 2004/0180086 | A1* | 9/2004 | Ramtoola et al. | A61K 9/2013 |
| 2005/0013863 | A1* | 1/2005 | Lim | A61K 31/4415 424/472 |
| 2009/0028941 | A1* | 1/2009 | Cowles | A61K 9/4808 514/338 |
| 2010/0112053 | A1* | 5/2010 | Momose | A61K 9/2086 514/567 |
| 2010/0305208 | A1* | 12/2010 | Dudhara | A61P 21/02 514/567 |
| 2012/0045485 | A1* | 2/2012 | Gan | A61K 31/00 427/2.21 |
| 2013/0217777 | A1* | 8/2013 | Kirkorian | A61K 9/2054 514/630 |
| 2014/0242168 | A1* | 8/2014 | Schiller | A61K 9/2886 514/263.34 |
| 2014/0348936 | A1* | 11/2014 | Reyes | A61K 9/20 514/159 |
| 2015/0231078 | A1* | 8/2015 | Gerard | A61K 9/2095 514/263.34 |
| 2016/0038411 | A1* | 2/2016 | Cowles | A61K 9/282 424/452 |
| 2016/0193155 | A1* | 7/2016 | Sharma | A61K 9/2095 424/463 |
| 2016/0256393 | A1* | 9/2016 | Gerard | A61K 9/2009 |
| 2017/0151189 | A1* | 6/2017 | Went | A61K 9/2846 |
| 2017/0172930 | A1* | 6/2017 | Berner | A61K 9/0002 |
| 2017/0319698 | A1* | 11/2017 | Vergnault | A61K 47/38 |

FOREIGN PATENT DOCUMENTS

| | | | | |
|---|---|---|---|---|
| JP | 7116044 | B2* | 12/1995 | A23L 33/115 |
| WO | WO-0015198 | A1* | 3/2000 | A61K 31/496 |
| WO | WO-0110419 | A1* | 2/2001 | A61K 9/0007 |
| WO | WO-0200213 | A1* | 1/2002 | A61K 31/663 |
| WO | WO-2004066981 | A1* | 8/2004 | A61K 31/421 |
| WO | WO-2008068731 | A1* | 6/2008 | A61K 31/403 |

OTHER PUBLICATIONS

S. H. Shaha, J. K. Patel, K. Pundarikakshudu, and N. V. Patel, "An overview of a gastro-retentive floating drug delivery system", Asian Journal of Pharmaceutical Sciences, 2009, 4(1): 65-80 (Year: 2009).*

Nayak, Amit Kumar, Jadupati Malakar, and Kalyan Kumar Sen, "Gastroretentive drug delivery technologies: Current approaches and future potential", Journal of Pharmaceutical Education and Research, 2010, 1(2): 1-12 (Year: 2010).*

Sigma Aldrich: Dibutyl Sebacate, obtained from the web at https:/Avww.sigmaaldrich.com/catalog/product/aldrich/d49504?lang=en&region=US on May 20, 2021 (Year: 2021).*

* cited by examiner

GASTRORETENTIVE DOSAGE FORMS FOR SUSTAINED DRUG DELIVERY

1. CROSS-REFERENCE TO RELATED APPLICATIONS

This application is a continuation of U.S. patent application Ser. No. 17/703,102, filed Mar. 24, 2022, which is a continuation of U.S. patent application Ser. No. 17/233,873, filed Apr. 19, 2021, which is a continuation of U.S. patent application Ser. No. 17/064,949, now U.S. Pat. No. 11,007,145, filed Oct. 7, 2020, which is a continuation of U.S. patent application Ser. No. 16/868,056, now U.S. Pat. No. 10,857,098, filed May 6, 2020, which is a continuation of U.S. patent application Ser. No. 16/319,086, now U.S. Pat. No. 10,918,597, filed Jan. 18, 2019, which is a U.S. National Stage Patent Application of PCT/US2018/038118, filed Jun. 18, 2018, which claims the benefit of priority to U.S. Provisional Patent Application No. 62/520,796, filed Jun. 16, 2017. The disclosures of all applications noted above are hereby incorporated by reference herein in their entireties.

2. FIELD OF THE INVENTION

The presently disclosed subject matter relates to gastroretentive oral dosage forms for modified release of active pharmaceutical agents. Such dosage forms are particularly beneficial for drugs having a narrow absorption window (NAW) in the upper gastrointestinal (GI) tract, weakly basic drugs that have high pH-dependent solubility, drugs that act locally in the upper GI tract, drugs that degrade in colon, or drugs that disturb normal colonic microbes.

3. BACKGROUND

Despite the advances in sustained release technology for pharmaceutical drugs, sustained release of active agents remains a challenge, including for example, moderately soluble drugs that have a relatively narrow absorption window in the GI tract (e.g., cimetidine, ranitidine, nizatidine, zolentine, metronidazole, timidazole, amoxicillin, minocycline, tetracycline, aspirin, p-aminobenzoic acid, somatostatin analogues, and levodopa/carbidopa). Many of the known sustained release technologies utilize hydrophilic, polymeric matrices that provide somewhat useful levels of control to the delivery of moderately and highly soluble drugs. Such matrices work to retain drugs in their dosage forms. However, for drugs of any level of solubility, the retention of the drug in a tablet or other dosage form beyond the duration of a fed mode/gastric emptying can reduce therapeutic efficacy of the drug.

In the absence of food, a dosage form can pass from the stomach into the small intestine, and over a period of 2 to 4 hours the dosage form passes through the small intestine, reaching the colon with the drug still in the dosage form. This can be problematic for drugs that would normally provide maximum benefit with minimum side effects when absorbed in the stomach and upper GI tract rather than the colon. If conditions are favorable in the stomach, they can be unfavorable in the colon. For example, most orally administered antibiotics have a potential of altering the normal flora of the gastrointestinal tract, and particularly the flora of the colon, resulting in release of dangerous toxins causing nausea, diarrhea, and life threatening or fatal side effects. Therefore, it would be most desirable to formulate the dosage form to release the drug before reaching the colon. Examples of soluble antibiotics that pose this type of threat are tetracycline, metronidazole, amoxicillin, and clindamycin.

Other challenges exist with certain drugs that are susceptible to degradation by intestinal enzymes. The degradation occurs before the drug can be absorbed through the intestinal wall, leaving only a fraction of the administered dose available for the intended therapeutic action. Examples of such drugs include ranitidine and metformin hydrochloride.

For certain drugs, acidic pH at a given site within the GI tract is an essential determinant of the bioavailability of the drug, as the solubility of the drug reduces with increasing pH. Such drugs may not be fully absorbed before reaching the colon because they require an acidic environment for providing effective bioavailability. Examples of highly soluble drugs that achieve their highest bioavailability at a low pH are esters of ampicillin. Some drugs that are soluble in an acidic environment but insoluble in an alkaline environment, lose their efficacy upon reaching the lower portions of the GI tract. For such drugs, portions of the drug that are undissolved cannot be absorbed, while the portions that are dissolved but not yet absorbed, can precipitate in small intestine.

Various gastroretentive systems known in the art are disclosed in the following documents: U.S. Pat. Nos. 4,101,650; 4,777,033; 4,844,905; PCT Publication Nos. WO 00/015198; WO 01/010419; WO 02/000213; Deshpande et al. (1997) *Int. J Pharmaceutics,* 159:255-258 ("Deshpande (1997a)"); and Deshpande et al. (1997) *Pharm. Res.,* 14(6): 815-819 ("Deshpande (1997b)"), the disclosures of which are herein incorporated by reference in their entireties.

Deshpande (1997a) evaluates various membranes with various ratios of EUDRAGIT® RL 30D and EUDRAGIT® NE 30D, used in the development of controlled release systems for gastric retention. The publication teaches that increasing amounts of EUDRAGIT® NE 30D have a normalizing effect on overall permeability of the membrane, while enhancing elasticity and mechanical strength of the membrane. The publication provides an optimum ratio of EUDRAGIT® RL 30D and EUDRAGIT® NE 30D as 70:30 in membranes for coating tablets. At this ratio, the combination provided enough elasticity to withstand pressure of expansion. However, the publication fails to address mutual noncompatibility of the two polymers, and its effect on the membrane strength to withstand pH and hydrodynamic conditions in stomach. The publication also fails to discuss the effects of such optimum ratios on release rate of drugs with various solubilities. Further, the publication fails to discuss or explain the effect of other EUDRAGIT polymers on membrane strength and membrane elasticity to withstand hydrodynamic conditions, while maintaining a desired release rate of the drug.

Deshpande (1997b) discloses gastroretentive tablets with a swelling core and a coating over the tablet core to provide support needed by the core to remain intact in shear stress and hydrodynamic environment of the GI tract. The swelling core of the gastroretentive tablets comprises CARBOPOL®, carbonates/bicarbonates, and a superdisintegrant, e.g., polyvinyl pyrrolidone XL. The tablets were noted to swell due to superdisintegrant-assisted disintegration of the tablet matrix; and gelling of CARBOPOL® in the presence carbonates/bicarbonates. Further, the release of $CO_2$ in the acidic pH of GI fluid confers buoyancy to the tablet.

Despite improvements in this area, there are only a handful of products that can take advantage of known gastroretentive systems due to inherent limitations, either due to the active pharmaceutical agent or suboptimal product design.

Thus, there remains a need in the art to extend the gastric residence time for certain drugs such that the drug is released into the proximity of its site of absorption (or action) for an sustained period or reaches other sites in the GI tract in a uniform manner. There is also a need in the art for rapidly expanding, modified release dosage forms with both high and low drug loading capacities that provide sustained release, or combined immediate and sustained release, of drugs that possess above-mentioned rationales for gastric retention. In particular, there is a need in the art for a modified release gastroretentive system that expands rapidly (expanding in about one hour or less to a size that prevents its passage through the pyloric sphincter) when in contact with gastric fluids, and remains in an expanded state for prolonged periods, e.g., about 8 to about 16 hours. The presently disclosed subject matter addresses these needs.

4. SUMMARY

The presently disclosed subject matter provides a floating gastroretentive dosage form comprising a matrix core that is a sustained release swellable matrix core comprising an active agent, a superdisintegrant, a water-soluble polymer, an acid, and a gas-generating agent; and a membrane that is a water-insoluble permeable elastic self-adjusting membrane comprising a plasticizer and at least one copolymer selected from the group consisting of ethyl acrylate, methylacrylate, and combinations. The membrane surrounds the matrix core. The floating gastroretentive dosage form provides sustained release of the active agent in a patient's stomach and swells at least about 200% in gastric fluid in about 30 minutes.

In certain embodiments, the dosage form is a tablet.

In certain embodiments, the active agent is a moderately soluble drug or a highly soluble drug. In certain embodiments, the active agent is selected from the group consisting of pyridostigmine, metaxalone, carvedilol, and a combination of carbidopa and levodopa.

In certain embodiments, the dosage form swells about 400% within about 45 minutes. In certain embodiments, the dosage form swells about 550% within about 60 minutes.

In certain embodiments, the superdisintegrant is selected from the group consisting of crospovidone; croscarmellose sodium; sodium starch glycolate; low substituted hydroxypropyl cellulose; microcrystalline cellulose; alginic acid; a mixture of 90% mannitol, 5% crospovidone, and 5% polyvinyl acetate; a coprocessed blend of mannitol, starch, crospovidone, croscarmellose sodium, colloidal silica, and silica. In certain embodiments, the superdisintegrant is crospovidone.

In certain embodiments, the water-soluble polymer in the matrix core is selected from the group consisting of hypromellose, hydroxypropyl cellulose, a polyethylene oxide polymer, a carbomer, and sodium alginate. In certain embodiments, the water-soluble polymer is hypromellose.

In certain embodiments, the gas-generating agent is a carbonate salt selected from the group consisting of $NaHCO_3$, $CaCO_3$, and a mixture thereof. In certain embodiments, the gas-generating agent is a mixture of $NaHCO_3$ and $CaCO_3$.

In certain embodiments, the plasticizer is selected from the group consisting of triethyl citrate, triacetin, polyethylene glycol, propylene glycol, and dibutyl sebacate. In certain embodiments, the plasticizer is triethyl citrate.

In certain embodiments, the copolymer comprises a copolymer of ethyl acrylate and methyl methacrylate, and/or a copolymer of ethyl acrylate, methyl methacrylate, and methacrylic acid ester with quaternary ammonium groups. In certain embodiments, the copolymer comprises a copolymer of ethyl acrylate and methyl methacrylate, and the copolymer of ethyl acrylate, methyl methacrylate, and methacrylic acid ester with quaternary ammonium groups in a ratio between 5:95 and 95:5. In certain embodiments, the ratio is between 10:90 and 90:10.

In certain embodiments, the copolymer comprises a copolymer of ethyl acrylate, methyl methacrylate, and methacrylic acid ester with quaternary ammonium groups.

In certain embodiments, the dosage form further comprises an immediate release layer comprising an immediate release active agent over the membrane.

In certain embodiments, the immediate release active agent comprises a combination of levodopa and carbidopa.

In certain embodiments, the dosage form further comprises a first seal coat between the matrix core and the membrane, and a second seal coat between the membrane and the immediate release layer.

In certain embodiments, the dosage form further comprises a third seal coat over the immediate release coat, and an overcoat over the seal coat.

In certain embodiments, the overcoat is the outermost coat.

In certain embodiments, the seal coat comprises a pH-independent water-soluble polymer comprising hypromellose or a polyvinyl acetate-based polymer. In certain embodiments, the seal coat comprises a polyvinyl acetate-based polymer.

In certain embodiments, the overcoat comprises a polyvinyl acetate-based polymer.

In certain embodiments, the dosage form in a swollen state is maintained until at least about 80% of the drug is released.

In certain embodiments, the gas-generating agent generates $CO_2$ independent of a fed or fasted state of an individual.

In certain embodiments, the dosage form exhibits a floating lag time of about 15 minutes or less.

The presently disclosed subject matter also provides a floating gastroretentive dosage form comprising a matrix core that is a sustained release, swellable matrix core comprising an active agent, a superdisintegrant, a water-soluble polymer, an acid, and a gas-generating agent; and a membrane that is a water-insoluble permeable elastic self-adjusting membrane comprising a plasticizer and at least one copolymer selected from the group consisting of ethyl acrylate, methylacrylate, and combinations thereof. The membrane surrounds the matrix core. The floating gastroretentive dosage form exhibits a floating lag time of about 15 minutes or less.

In certain embodiments, the dosage form is a tablet.

In certain embodiments, the active agent is selected from the group consisting of pyridostigmine, metaxalone, carvedilol, and a combination of carbidopa and levodopa.

In certain embodiments, the dosage form exhibits a floating lag time of about 12 minutes or less.

In certain embodiments, the superdisintegrant is crospovidone.

In certain embodiments, the water-soluble polymer is hypromellose.

In certain embodiments, the gas-generating agent is $NaHCO_3$ and/or $CaCO_3$.

In certain embodiments, the plasticizer is triethyl citrate.

In certain embodiments, the copolymer comprises a copolymer of ethyl acrylate and methyl methacrylate, and/or a copolymer of ethyl acrylate, methyl methacrylate, and methacrylic acid ester with quaternary ammonium groups.

In certain embodiments, the copolymer comprises a copolymer of ethyl acrylate and methyl methacrylate, and a copolymer of ethyl acrylate, methyl methacrylate, and methacrylic acid ester with quaternary ammonium groups in a ratio of between 10:90 and 90:10.

In certain embodiments, the copolymer comprises a copolymer of ethyl acrylate, methyl methacrylate, and methacrylic acid ester with quaternary ammonium groups.

In certain embodiments, the dosage form further comprises an immediate release layer comprising an immediate release active agent over the membrane.

In certain embodiments, the immediate release active agent comprises a combination of levodopa and carbidopa.

In certain embodiments, the gas-generating agent generates $CO_2$ independent of a fed or fasted state of an individual.

In certain embodiments, the dosage form swells about 200% within about 30 minutes. In certain embodiments, the dosage form swells about 550% within about 60 minutes.

5. BRIEF DESCRIPTION OF THE DRAWINGS

Figure 7:
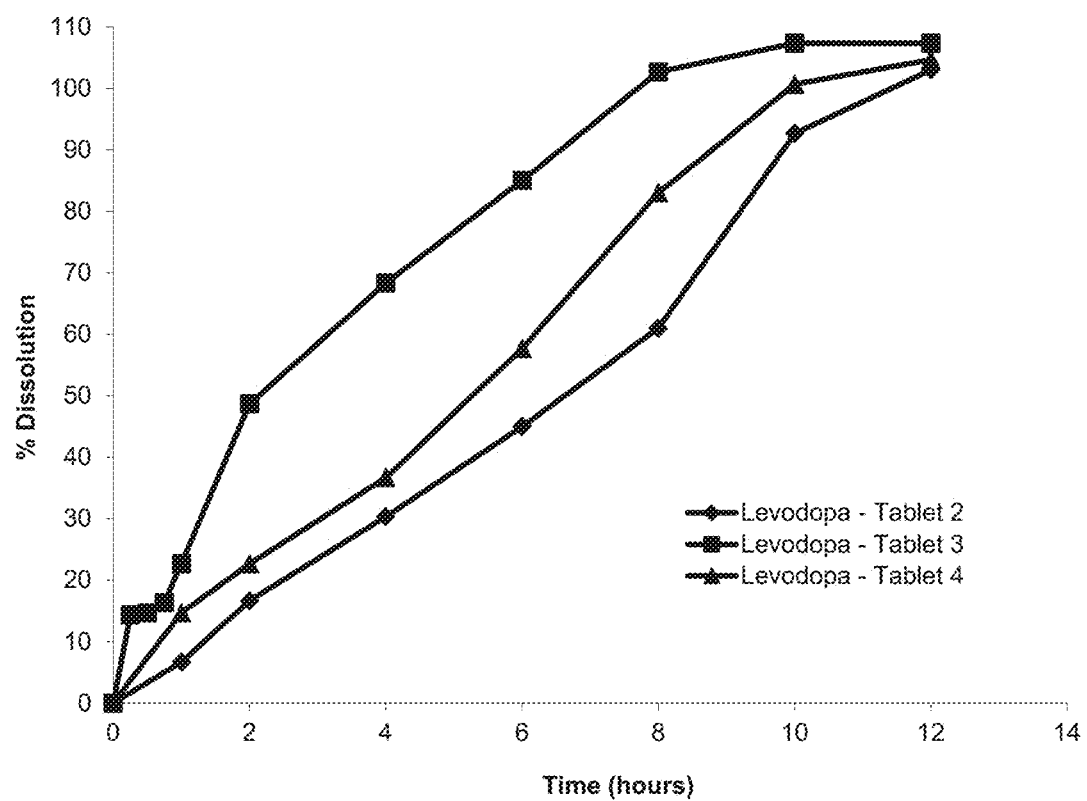

FIG. 7 shows rotating bottle cyclic dissolution profile of Levodopa Tablets 2, 3, and 4, at 15 rpm, with initial dissolution in 200 ml 0.01N HCl for 4 hours, followed by dissolution in pH 4.5 acetate buffer for 4 hours, and final dissolution in 0.01N HCl for 4 hours.

Figure 8:
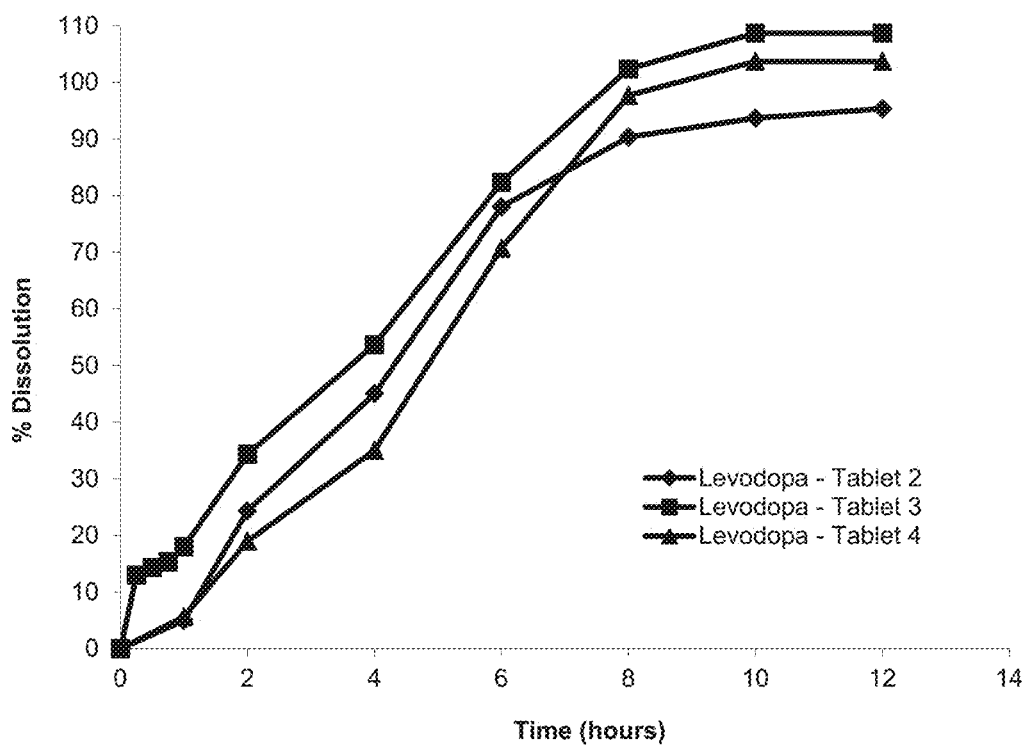

FIG. 8 shows rotating bottle cyclic dissolution profile of Levodopa Tablets 2, 3, and 4, at 15 rpm, with initial dissolution in 200 ml pH 4.5 acetate buffer for 4 hours, followed by dissolution in 0.01N HCl for 4 hours, and final dissolution in pH 4.5 acetate buffer for 4 hours.

Figure 9:
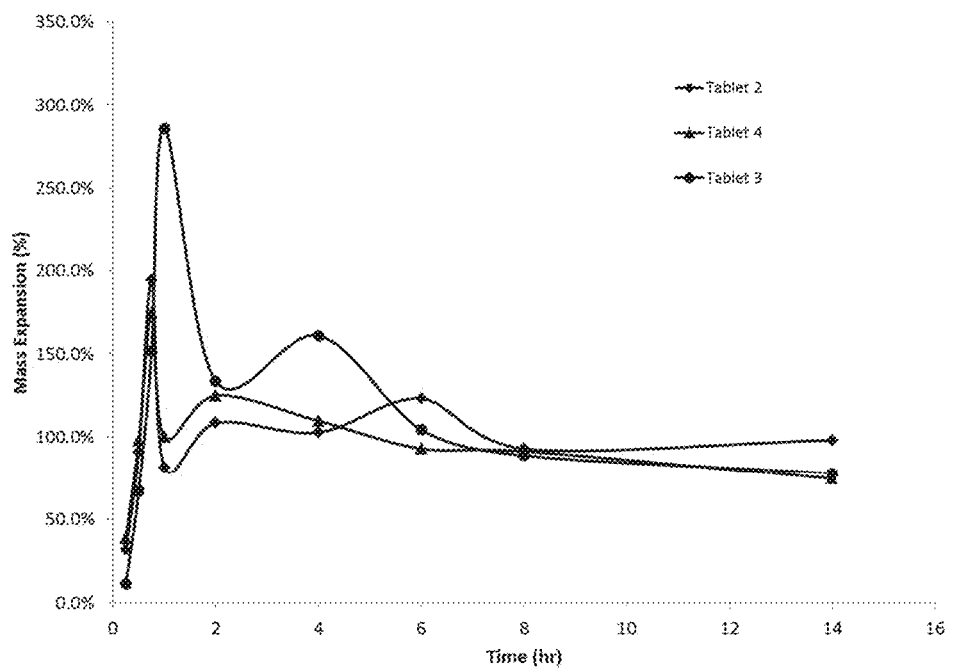

FIG. 9 shows gravimetric swelling of Levodopa Tablets 2, 3, and 4, in 0.01N HCl.

Figure 10:
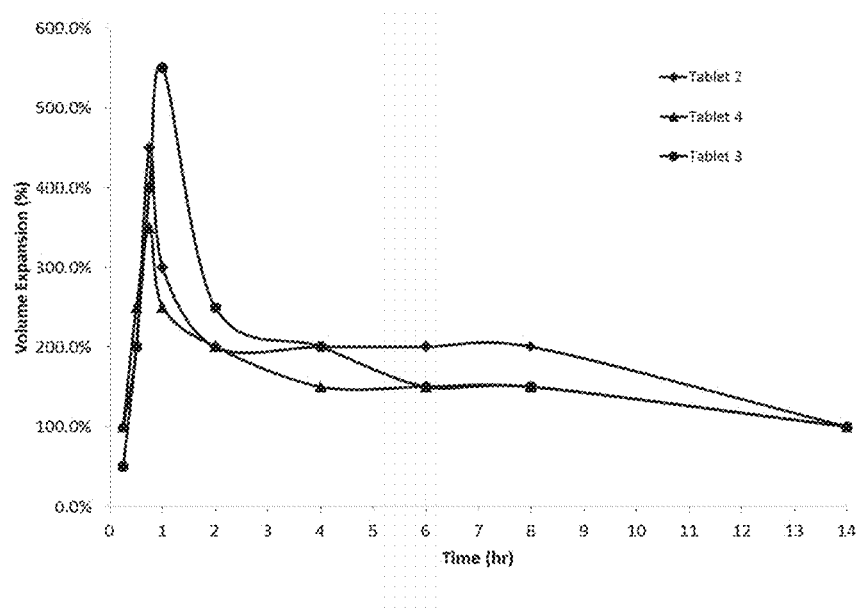

FIG. 10 shows volumetric swelling of Levodopa Tablets 2, 3, and 4, in 0.01N HCl.

Figure 11:
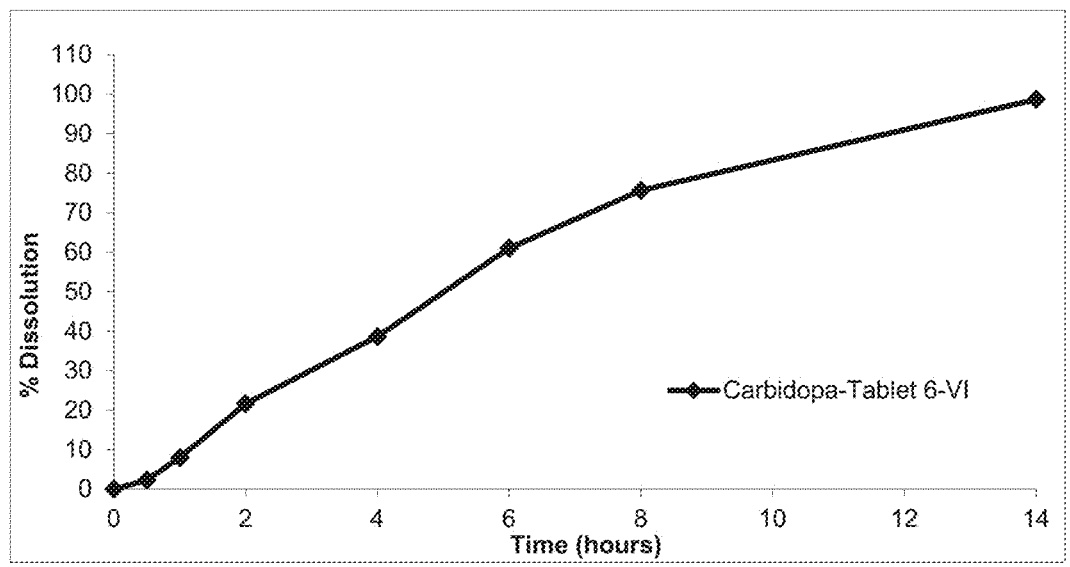

FIG. 11 shows rotating bottle dissolution profiles of Carbidopa from Tablet 6-VI at 15 rpm, in 200 ml pH 4.5 acetate buffer.

Figure 12:
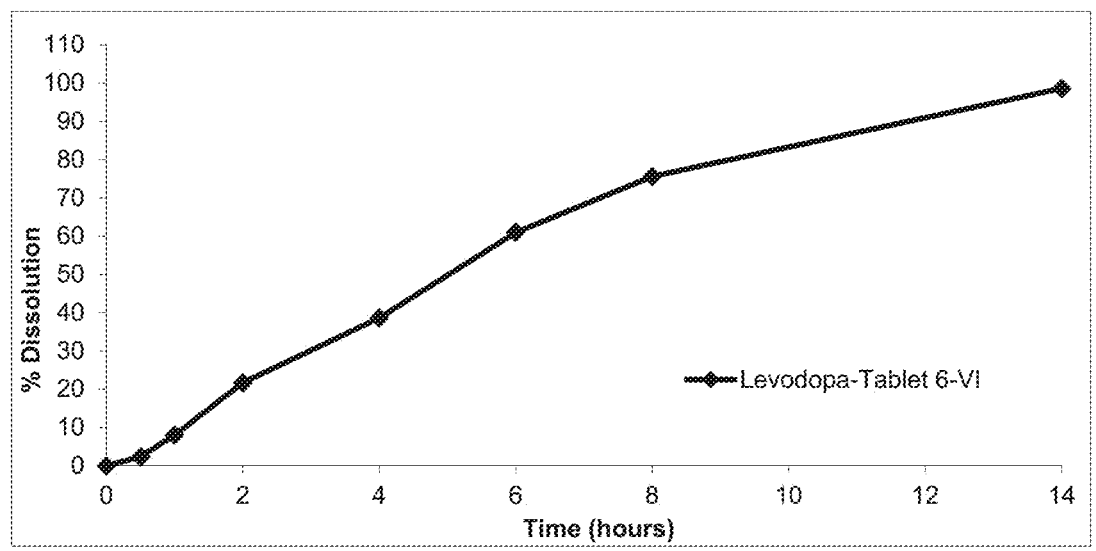

FIG. 12 shows rotating bottle dissolution profiles of Levodopa from Tablet 6-VI at 15 rpm, in 200 ml pH 4.5 acetate buffer.

Figure 13:
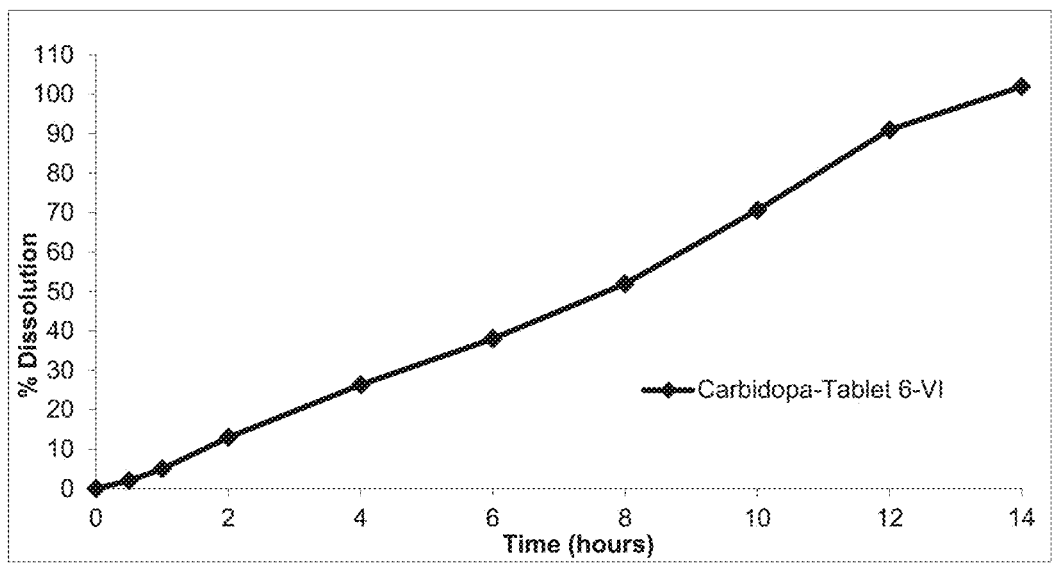
Figure 14:
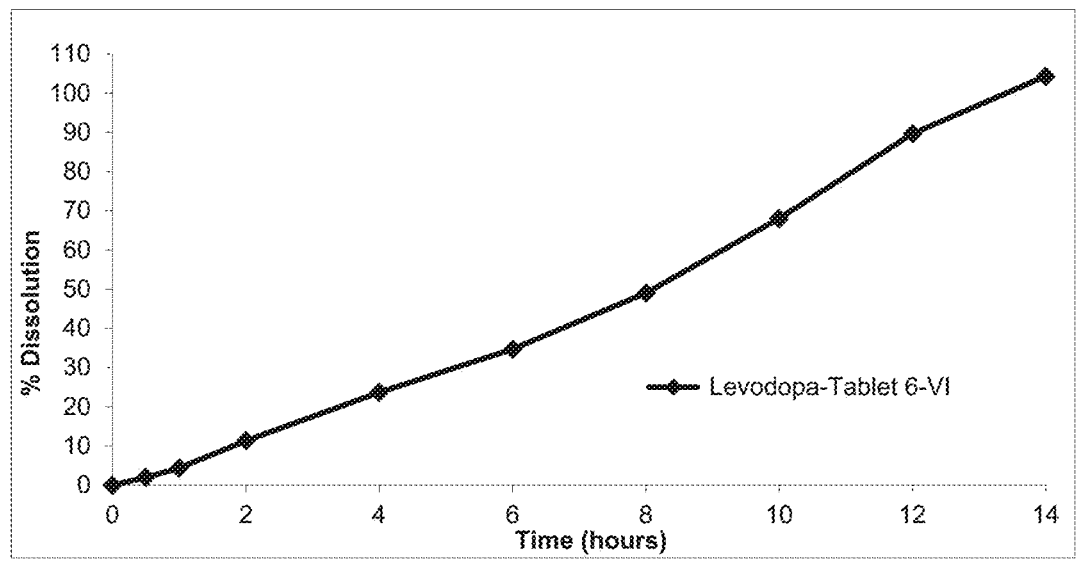

FIG. 13 shows biodisk reciprocating cylinder apparatus dissolution profiles of Carbidopa from Tablet 6-VI at 25 dpm, in 200 ml pH 4.5 acetate buffer FIG. 14 shows biodisk reciprocating cylinder apparatus dissolution profiles of Levodopa from Tablet 6-VI at 25 dpm, in 200 ml pH 4.5 acetate buffer.

Figure 15:
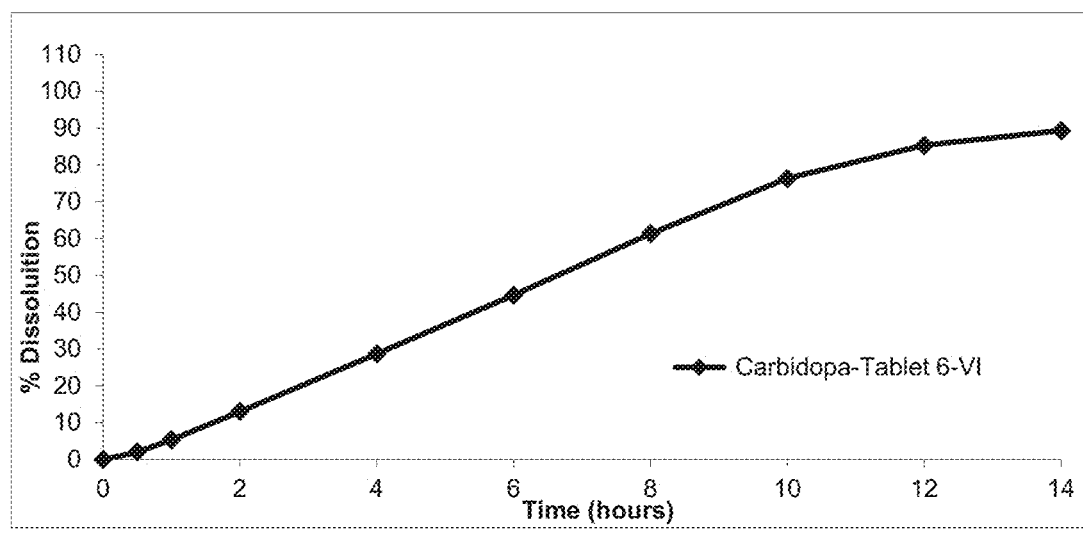

FIG. 15 shows custom basket (40 mesh) dissolution profiles of Carbidopa from Tablet 6-VI at 100 rpm, in 900 ml pH 4.5 acetate buffer.

Figure 16:
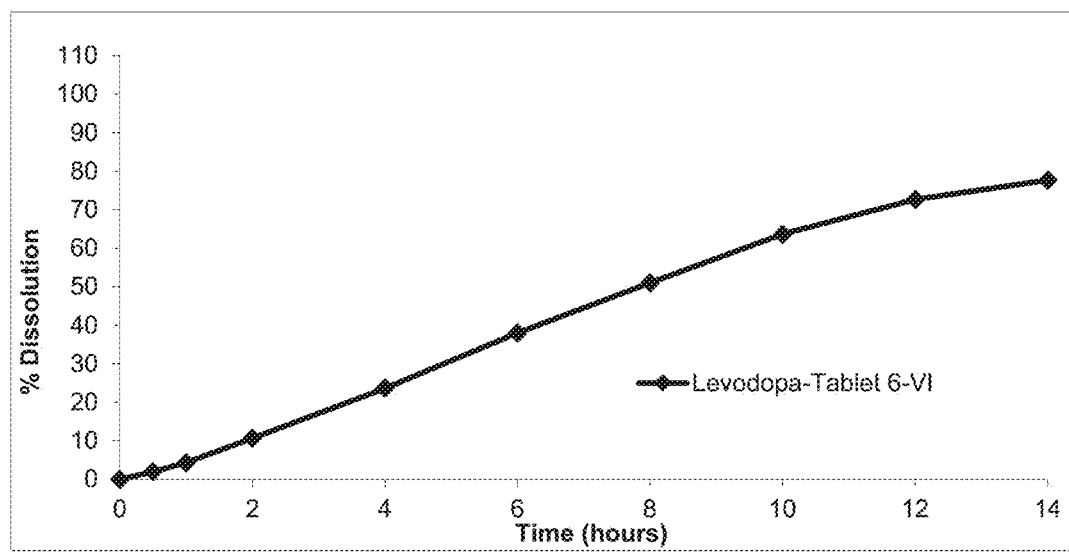

FIG. 16 shows custom basket (40 mesh) dissolution profiles of Levodopa from Tablet 6-VI at 100 rpm, in 900 ml pH 4.5 acetate buffer.

Figure 17:
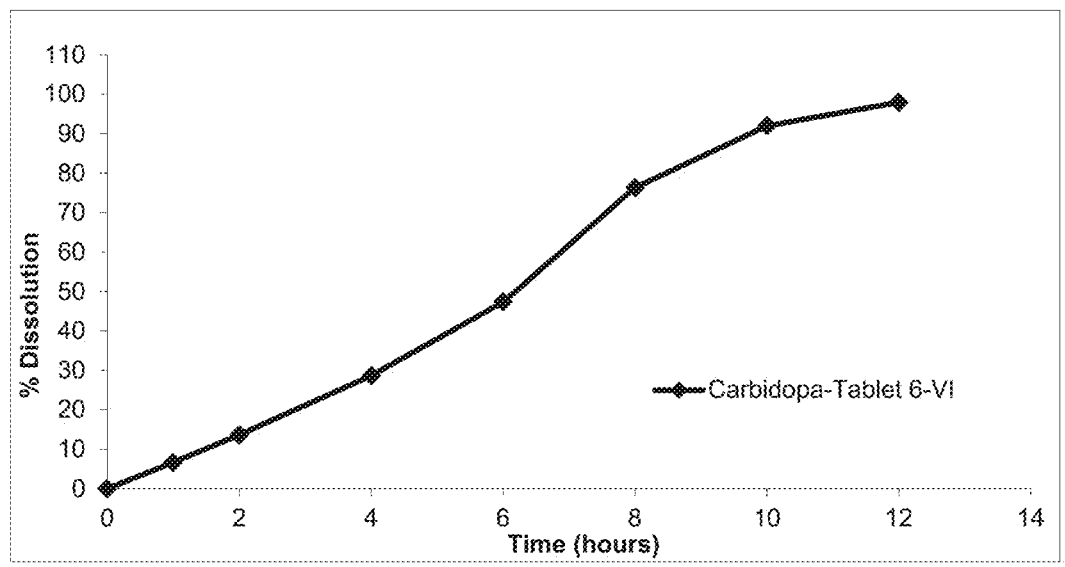

FIG. 17 shows biodisk reciprocating cylinder apparatus dissolution profiles of Carbidopa from Tablet 6-VI at 25 dpm, in 200 ml pH 4.5 acetate buffer for 4 hours, followed by dissolution in 0.01N HCl for 4 hours, and final dissolution in pH 4.5 acetate buffer for 4 hours.

Figure 18:
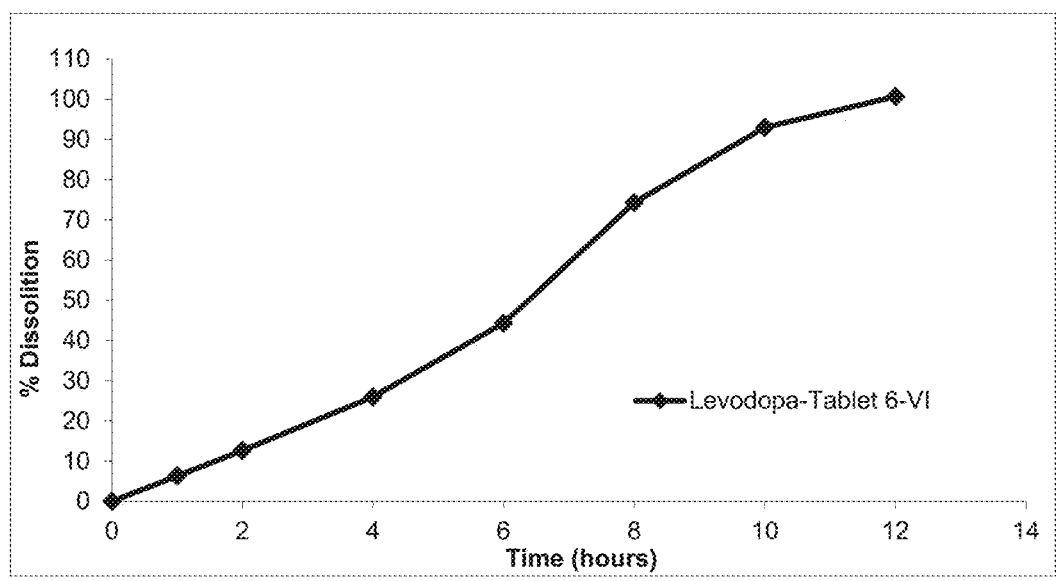

FIG. 18 shows biodisk reciprocating cylinder apparatus dissolution profiles of Levodopa from Tablet 6-VI at 25 dpm, in 200 ml pH 4.5 acetate buffer for 4 hours, followed by dissolution in 0.01N HCl for 4 hours, and final dissolution in pH 4.5 acetate buffer for 4 hours.

Figure 19:
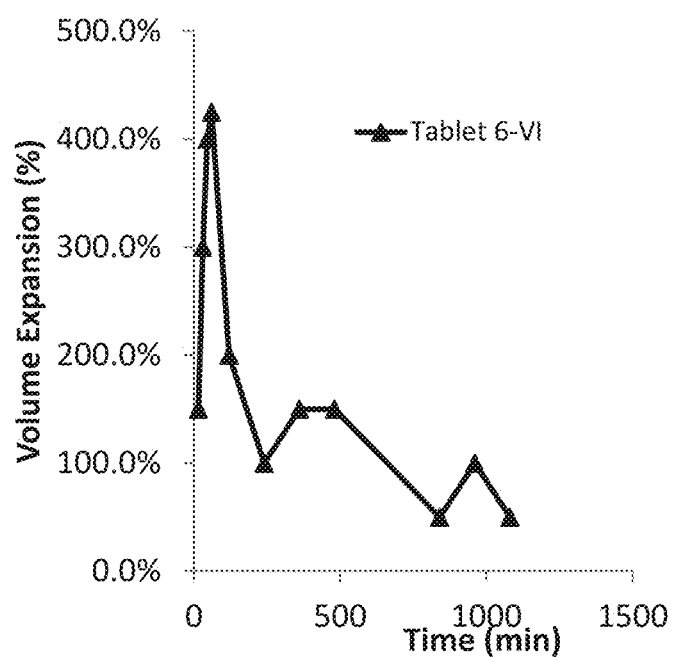

FIG. 19 shows volumetric swelling of Levodopa/Carbidopa Tablet 6-VI, measured in a rotating bottle apparatus, at 15 rpm, in pH 4.5 acetate buffer.

Figure 20:
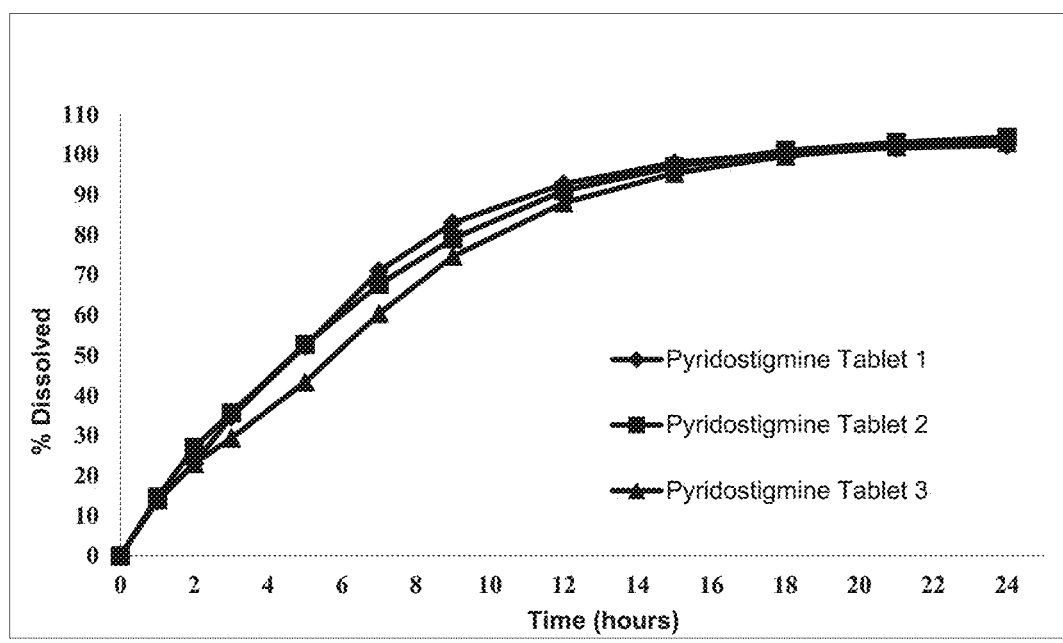

FIG. 20 shows custom basket dissolution profiles of pyridostigmine bromide from Pyridostigmine Tablets 1, 2, and 3.

6. DETAILED DESCRIPTION

The presently disclosed subject matter provides gastroretentive dosage forms that maximize the bioavailability of various drugs having rationales for gastroretentive administration. In particular, the dosage forms provide for gastroretentive administration of drugs having variable transit times through various regions of the GI tract, have narrow absorption window in the regions of GI tract, are susceptible to degradation in alkaline environment, require acidic environment for maximum solubility, and/or are precipitated in alkaline environment. Gastroretentive dosage forms of the disclosure provide an improved pharmacokinetic profile by retaining the dosage form in the stomach for a prolonged period of time. Prolonged gastric retention improves bioavailability, reduces drug waste, and improves solubility of drugs that are less soluble in a high pH environment.

For clarity and not by way of limitation, this detailed description is divided into the following subportions:

6.1. Definitions;
6.2. Gastroretentive Dosage Forms;
6.3. Features of the Dosage Forms; and
6.4. Active Agents.

6.1 Definitions

The terms used in this specification generally have their ordinary meanings in the art, within the context of this invention and in the specific context where each term is used. Certain terms are discussed below, or elsewhere in the specification, to provide additional guidance to the practitioner in describing the compositions and methods of the invention and how to make and use them.

As used herein, the use of the word "a" or "an" when used in conjunction with the term "comprising" in the claims and/or the specification may mean "one," but it is also consistent with the meaning of "one or more," "at least one," and "one or more than one." Still further, the terms "having," "including," "containing" and "comprising" are interchangeable and one of skill in the art is cognizant that these terms are open ended terms.

The term "about" or "approximately" as used herein means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

The terms "active agent" and "drug," as used interchangeably herein, refer to an active pharmaceutical ingredient (API) compound, composition of matter, or mixture thereof that provides a therapeutic or prophylactic effect in the treatment of a disease or abnormal physiological condition. Examples of highly soluble drugs to which this disclosure is applicable are pyridostigmine, metformin hydrochloride, vancomycin hydrochloride, captopril, erythromycin lactobionate, ranitidine hydrochloride, sertraline hydrochloride, ticlopidine hydrochloride, amoxicillin, cefuroxime axetil, clindamycin, doxifluridine, tramadol, fluoxitine hydrochloride, ganciclovir, bupropion, lisinopril, and esters of ampicillin. Examples of moderately soluble drugs to which this disclosure is applicable are cefaclor, ciprofloxacin, carbidopa, levodopa, saguinavir, ritonavir, nelfinavir, ceftazidine, cyclosporine, digoxin, paclitaxel, iron salts, topiramate, and ketoconazole. Drugs of particular interest are carbidopa, levodopa, pyridostigmine, and metformin hydrochloride. The drug loadings (weight percent of drug relative to total of drug and polymer) in most of these cases will be about 80% or less.

The term "degradable," as used herein, refers to capable of being chemically and/or physically modified, dissolved, or broken down, e.g., in the body of a patient, within a relevant time period.

The term "diffusion," as used herein, refers to "passive diffusion" comprising movement of molecules down their concentration gradient.

The term "dissolution lag time," as used herein, includes the time between the addition of a dosage form to a medium and the time when the active agent begins to dissolve in the medium (e.g., in an in vitro setting), or the time between the consumption of a dosage form by a user and the time when the dosage form begins to dissolve in the gastric fluid (e.g., in an in vivo setting).

The term "dosage" is intended to encompass a formulation expressed in terms of μg/kg/day, μg/kg/hr, mg/kg/day or mg/kg/hr. The dosage is the amount of an ingredient administered in accordance with a particular dosage regimen. A "dose" is an amount of an agent administered to a mammal in a unit volume or mass, e.g., an absolute unit dose expressed in mg or μg of the agent. The dose depends on the concentration of the agent in the formulation, e.g., in moles per liter (M), mass per volume (m/v), or mass per mass (m/m). The two terms are closely related, as a particular dosage results from the regimen of administration of a dose or doses of the formulation. The particular meaning in any case will be apparent from context.

The term "erosion," as used herein with respect to polymer matrix core, refers to a decrease in size of the matrix core due to dissolution of polymers from the polymer matrix core beyond polymer gel-solution interface. In particular, the term "erosion" refers to dissolution of polymer beyond polymer gel-solution interface where the polymer has become sufficiently dilute that it can be transported away from the polymer matrix via diffusion across the membrane.

The terms "expanding" and "expansion," as used herein with respect to a polymeric membrane, refer to stretching or distention of a membrane due to the presence of at least one plasticizer, and an outward pressure, e.g., gas pressure, on the membrane. The term "rapidly expanding" as used herein with respect to a polymeric membrane, refers to expansion of the membrane being faster than swelling of the matrix core due to imbibition of fluid. In certain embodiments, the term "rapidly expanding" refers to expansion of membrane to provide at least about a 200% volume gain of the dosage form from its initial volume in about 30 minutes.

As used herein, "floating" is used in conjunction with a "floating gastroretentive dosage form" which has a bulk density less than gastric fluids. Such dosage forms are "floating" in that they remain buoyant in the gastric fluids of the stomach for a targeted period of time. The floating dosage form then is able to be retained in the stomach, while releasing an active agent.

The term "floating lag time," as used herein, includes the time between the addition of a dosage form to a medium and the time when the dosage form begins to float on the medium (e.g., in an in vitro setting), or the time between the consumption of a dosage form by a user and the time when the dosage form begins to float on the surface of the gastric fluid (e.g., in an in vivo setting).

The phrases "gastric medium," "simulated gastric fluid," "simulated intestinal fluid," "intestinal medium," and the like, as used herein, refer to media occurring in stomach and in intestines, correspondingly, or to the solutions that are used to mimic their chemical environment in vitro. As used herein, the term "dissolution medium" refers to a medium used to mimic pH of gastric fluid in fed or fasted state of an individual. In certain embodiments, the medium used to mimic fed state of an individual includes pH 4.5 acetate buffer; and the medium used to mimic fasted state of an individual includes 0.01 N HCl.

The phrase "gastroretentive dosage form," used herein interchangeably with "gastroretentive oral floating drug delivery system," "gastroretentive formulation," or the like, refers to modified release dosage forms providing delayed gastric emptying as compared to food (e.g., retention in the stomach beyond the retention of food).

The term "modified release" or "MR" refers to dosage forms that are formulated to alter timing and/or rate of release of the drug substance from that of conventional dosage form (e.g., immediate release). The modified release dosage forms of the disclosure can include delayed release (DR), extended release (ER), controlled release (CR), target release (TR), and controlled sustained release (CR/SR) dosage forms.

As used herein, the term "oral floating" refers to a floating gastroretentive dosage form that is consumed orally.

The term "patient" or "subject" as used herein, refers to a human or nonhuman mammal that is in need or may be in need to receive a gastroretentive dosage form of the present disclosure.

The term "permeable," as used herein, refers to a membrane containing sparingly soluble polymers with or without a pore former, or insoluble polymer, with a pore former, that will allow a controlled flow of particles/fluids through the membrane by diffusion. As used herein, the terms functional coat and permeable membrane are used interchangeably.

The term "pharmaceutically acceptable," when used in connection with the pharmaceutical compositions of the invention, refers to molecular entities and compositions that are physiologically tolerable and do not typically produce untoward reactions when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, dispersing agent or vehicle with which the compound is administered. Such pharmaceutical carriers can be sterile liquids, such as water and oils. For example, water, aqueous solutions, saline solutions, aqueous dextrose or glycerol solutions can be employed as carriers, particularly for injectable solutions. Suitable pharmaceutical carriers are described in, for example, "Remington's Pharmaceutical Sciences" by Philip P. Gerbino, 21st Edition (or previous editions).

The term "pharmaceutical composition" as used in accordance with the present invention relates to compositions that can be formulated in any conventional manner using one or more pharmaceutically acceptable carriers or excipients. A "pharmaceutically acceptable" carrier or excipient, as used herein, means approved by a regulatory agency of the Federal or a state government, or as listed in the U.S. Pharmacopoeia or other generally recognized pharmacopoeia for use in mammals, and more particularly in humans.

The terms "pore former" and the like, as used herein, refer to water-soluble polymers and/or water-soluble small molecules that will form pores or channels (i.e., behave as a channeling agent) in the membrane, thereby creating a permeable membrane.

The phrase "prolonged period" or the like, as used herein, refers to a period of delivery that lasts for about an hour to several hours, including, for example from about 1 hour to about 24 hours, or alternatively from about 5 hours to about 18 hours, or from about 5 hours to about 16 hours. A prolonged period (or the like) can include any incremental time frame between 1 hour and 24 hours, including 1, 2, 3, 4, 5, 6, 7, 8, 9, 10, 11, 12, 13, 14, 15, 16, 17, 18, 19, 20, 21, 22, 23, or 24 hours. In alternative embodiments, the prolonged period can be over 24 hours.

The terms "shear" and "shear effect," as used interchangeably herein, refer to peristaltic waves moving from the midcorpus of the stomach to the pylorus.

In certain embodiments, "solubility" is defined in terms of ability to dissolve in water. The term "highly soluble" includes drugs with a solubility of greater than 100 mg/ml water; the term "moderately soluble" includes drugs with a solubility of between 100 mg/ml and 1 mg/ml of water; the term "sparingly soluble" includes drugs with a solubility of between 1 mg/ml and 0.1 mg/ml of water.; and the term "insoluble" includes drugs with a solubility of less than 0.1 mg/ml of water.

The terms "swellable" and "swelling," as used herein with respect to a polymer in the matrix core, refer to a polymer capable of imbibing fluid and swelling when in contact with a fluid environment.

The terms "therapeutically effective dose," "effective amount," and "therapeutically effective amount" refer to an amount sufficient to produce the desired effect. In some nonlimiting embodiments, a "therapeutically effective dose" means an amount sufficient to reduce by at least about 15%, preferably by at least about 50%, more preferably by at least about 90%, and most preferably prevent, a clinically significant deficit in the activity, function and response of the host. Alternatively, a therapeutically effective amount is sufficient to cause an improvement in a clinically significant condition in the host. These parameters will depend on the severity of the condition being treated, other actions, such as diet modification, that are implemented, the weight, age, and sex of the subject, and other criteria, which can be readily determined according to standard good medical practice by those of skill in the art. In other non-limiting embodiments, a therapeutic response may be any response that a user (e.g., a clinician) will recognize as an effective response to the therapy. Thus, a therapeutic response will generally be an induction of a desired effect.

The terms "treating" and "treatment," as used herein, refer to obtaining a desired pharmacological and physiological effect. The effect can be prophylactic in terms of preventing or partially preventing a disease, symptom, or pathological condition and/or can be therapeutic in terms of a partial or complete alleviation or cure of a disease, condition, symptom, or adverse effect attributed to a pathological condition. Thus, "treatment" (and the like) covers any treatment of a disease in a mammal, particularly in a human, and includes, but is not limited to: (a) preventing a pathological condition from occurring in an individual who can be predisposed to develop the condition but, e.g., has not yet been diagnosed as having such condition (e.g., causing the clinical symptoms of such condition not to develop); (b) inhibiting, arresting, or reducing the development of the pathological condition or its clinical symptoms; and (c) relieving symptoms associated with the pathological condition.

The term "upper GI tract," as used herein, includes the stomach, duodenum, and proximal small intestine.

6.2 Gastroretentive Dosage Forms

The presently disclosed subject matter provides for novel and nonobvious gastroretentive dosage forms. The disclosed dosage forms include:
 (i) a sustained release swellable matrix core, which comprises an active agent, a superdisintegrant, and a water-soluble polymer, and
 (ii) a water-insoluble permeable elastic membrane surrounding the matrix core, wherein the membrane comprises a plasticizer and at least one copolymer.

In certain embodiments, the gastroretentive oral floating dosage form includes
 (i) a sustained release core comprising a drug, a superdisintegrant, a water-soluble polymer, e.g., hypromellose, that swells via imbibition of water from gastric fluid to increase the size of the dosage form to promote gastric retention, and a gas-generating agent to promote floatation of the dosage form, the core being capable of swelling and achieving floatation rapidly (e.g., in about less than 15 minutes) while maintaining its physical integrity in GI fluids for prolonged periods of about 8-16 hours;
 (ii) a seal coat over the core, comprising a pH-independent water-soluble polymer to provide additional support to the core to maintain its physical integrity; and
 (iii) a rapidly expanding water-insoluble permeable elastic membrane over the seal coat providing desired characteristics for drug release and mechanical strength. In certain embodiments, the dosage form of the disclosure provides membrane controlled release. In certain embodiments, the dosage form of the disclosure contains an additional amount of the drug applied as a quick dissolving immediate-release layer on the outside of the particle or tablet. This layer is referred to as a "loading dose" and it is included for immediate release into the patient's bloodstream upon ingestion of the dosage form. The "loading dose" is high enough to quickly raise the blood concentration of the drug but not high enough to produce overdosing.

In accordance with another embodiment of the disclosure, the oral floating gastroretentive dosage form that continues to swell and eventually loses its integrity after a substantial amount of drug has been released to enable the passage of the essentially empty shell/membrane from the stomach comprises: (i) a sustained release matrix core comprising an active agent, a superdisintegrant, a water-soluble polymer that swells via imbibition of water from gastric fluid, an acid, and a gas-generating agent, and (ii) a permeable elastic membrane over the matrix core comprising at least one copolymer based on ethyl acrylate and methyl methacrylate, a plasticizer, and a surfactant. The system swells rapidly, e.g., in less than about 30 minutes, either in the fed or fasted state, to a size that prevents its passage through the pyloric sphincter, and the membrane, under either fed or fasted conditions, maintains the integrity of the system in a swollen state for prolonged periods of time, e.g., about 1-24 hours, e.g., at least about 8-16 hours, under hydrodynamic conditions created by gastric motility (shear effect) and pH variations.

Figure 1:
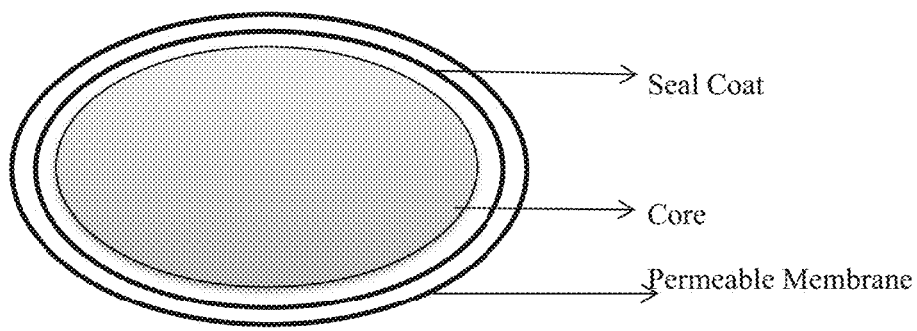
FIG. 1 depicts a schematic representation of the gastroretentive dosage form according to certain embodiments.

For the purpose of illustration and not limitation, FIG. 1 provides a schematic representation of the gastroretentive dosage form according to certain embodiments illustrating the matrix core, the seal coat and the permeable membrane.

Swellable Matrix Core

The swellable matrix core of the disclosed subject matter comprises an active agent, superdisintegrant, and water soluble polymer.

In certain embodiments, the tablet core comprises an acid to achieve rapid floating and expansion of the tablet, and for providing modified release of the active ingredient. In certain embodiments, the modified release is sustained release. In certain embodiments, the active agent in the core is the same as the active agent in the immediate release layer. In certain embodiments, the active agent in the immediate release layer is different from that found in the core. In certain embodiments, an overcoat surrounds the permeable membrane/functional coat or the immediate release layer. In certain embodiments, the immediate release layer is surrounded by a seal coat and an overcoat, wherein the overcoat is the outermost layer.

Disintegrants are substances or mixtures of substances added to the drug formulation that facilitate the breakup or disintegration of the tablet or capsule contents into smaller particles that dissolve more rapidly than in the absence of disintegrant. Superdisintegrants are generally used at a low level in the solid dosage form, typically about 1 to about 10% by weight relative to the total weight of the dosage unit. Examples of superdisintegrants in accordance with the present disclosure include, but are not limited to, croscarmellose sodium; sodium starch glycolate; low substituted hydroxypropyl cellulose; crospovidone; a mixture of 90% mannitol, 5% crospovidone, and 5% polyvinyl acetate (LUDI-FLASH®); a coprocessed blend of mannitol, starch, crospovidone, croscarmellose sodium, colloidal silica, and silica (PHARMABURST®); microcrystalline cellulose; and alginic acid. In certain embodiments, the superdisintegrant is crospovidone.

The water-swellable polymer forming the matrix in accordance with this disclosure is any polymer that is nontoxic, that swells upon imbibition of water, and that provides for sustained release of an incorporated drug. Examples of polymers suitable for use in this disclosure are cellulose polymers and their derivatives (e.g., hypromellose, hydroxyethyl cellulose, hydroxypropyl cellulose, carboxymethylcellulose, and microcrystalline cellulose, polysaccharides and their derivatives, polyalkylene oxides, polyethylene glycols, alginates, chitosan, poly(vinyl alcohol), xanthan gum, maleic anhydride copolymers, poly(vinyl pyrrolidone), starch and starch-based polymers, poly (2-ethyl-2-oxazoline), poly(ethyleneimine), polyurethane hydrogels, and cross-linked polyacrylic acids and their derivatives.

In certain embodiments, the matrix core further comprises gas-generating agents, e.g., carbonate and bicarbonate salts, that generate $CO_2$ in presence of acidic gastric fluid. In certain embodiments, the matrix core further comprises organic and/or inorganic acids that react with carbonate salts in an aqueous environment, e.g., at neutral pH or at a weekly acidic pH, and generate $CO_2$ gas. In certain embodiments, the acids include, but are not limited to, succinic acid, citric acid, acetic acid, malic acid, fumaric acid, stearic acid, tartaric acid, boric acid, and benzoic acid. In certain embodiments, combinations of acids can be used, including combinations of the above-listed acids.

In certain embodiments, gas-generating agents are the agents that generate $CO_2$ on interaction with acid. Examples of gas-generating agents that can be used in the formulations of the present disclosure include, but are not limited to, all organic and inorganic strong and weak bases, e.g., carbonate and bicarbonate salts of alkali and alkaline earth metals, that can interact with stomach acid for in situ gas generation. In certain embodiments, the gas-generating agent is sodium bicarbonate, sodium carbonate, magnesium carbonate, and/or calcium carbonate. In certain embodiments, the acid is succinic acid.

In certain embodiments, the oral floating gastroretentive dosage forms contain at least one acid and a gas-generating agent in the tablet core to provide a floating lag time, independent of the pH of the stomach of an individual, of less than about 15 minutes.

Permeable Elastic Membrane

The disclosed dosage forms comprise a water-insoluble permeable elastic membrane surrounding the matrix core, wherein the membrane comprises a plasticizer and at least one copolymer based on ethyl acrylate and methyl methacrylate.

Plasticizers provide self-adjusting ability to the permeable elastic membrane. Plasticizers provide elasticity to the membrane, ensuring that the membrane does not rupture upon expanding and that the system provides the desired characteristics for drug release, hydrodynamic balance, and mechanical strength to withstand variations in pH and shear in the stomach during fed and fasted conditions. In some embodiments, as dissolution of the active agent in the matrix proceeds, the plasticizer leaches out of the membrane; this causes the membrane to become brittle, which leads to rupture of the membrane. Hydrophilic plasticizers suitable for the disclosure include, but are not limited to, glycerin, polyethylene glycols, polyethylene glycol monomethyl ether, propylene glycol, and sorbitol sorbitan solution. Hydrophobic plasticizers suitable for the disclosure include, but are not limited to, acetyl tributyl citrate, acetyl triethyl citrate, castor oil, diacetylated monoglycerides, dibutyl sebacate, diethyl phthalate, triacetin, tributyl citrate, triethyl citrate, gelucire 39/01, and gelucire 43/01. In certain embodiments of the disclosure, the plasticizers include various polyethylene glycols, glycerin, and triethyl citrate. In a preferred embodiment of the disclosure, the plasticizer is triethyl citrate.

In certain embodiments of the disclosure, the permeable elastic membrane is formed from a combination of two (or more) polymers: at least one of EUDRAGIT® RL 30D (copolymer dispersion of ethyl acrylate, methyl methacrylate, and methacrylic acid ester with quaternary ammonium groups, 1:1:0.1) and EUDRAGIT® RS 30D (copolymer dispersion of ethyl acrylate, methyl methacrylate, and methacrylic acid ester with quaternary ammonium groups, 1:2: 0.1) to improve permeability, and at least one of KOLLICOAT® SR 30D (dispersion of polyvinyl acetate and polyvinyl pyrolidone), EUDRAGIT® NE 30D (copolymer dispersion of ethyl acrylate, methyl methacrylate), and EUDRAGIT® NM 30D (copolymer dispersion of ethyl acrylate, methyl methacrylate), to improve mechanical strength (tensile strength). The membrane can further include a plasticizer, hydrophilic polymers and, optionally, water soluble nonionic polymers that act as pore formers, to modify its elasticity, permeability, and tensile strength.

In certain embodiments of the disclosure, a permeable elastic membrane over the tablet core provides desired characteristics for drug release and tensile strength to withstand peristalsis and mechanical contractility of the stomach (shear). The combination of a water-soluble polymer, e.g., hypromellose, in the tablet core, and the unique permeable elastic membrane formed over the matrix core by the coating of a homogeneous dispersion of at least one of EUDRAGIT® RL 30D and EUDRAGIT® RS 30D (collectively "dispersions of ammonium salts of copolymers") to improve permeability, and at least one of KOLLICOAT® SR 30D, EUDRAGIT® NE 30D, and EUDRAGIT® NM 30D (collectively "neutral copolymer dispersions") to improve mechanical strength (tensile strength), provides the desired controlled drug release while maintaining the integrity of the tablet core in an expanded state, thus extending the gastric residence time and preventing the dosage form from being emptied from the stomach until substantial or complete release of the drug, usually after a prolonged period. In certain embodiments, at least one of EUDRAGIT® RL 30D and EUDRAGIT® RS 30D is present in a ratio with KOLLICOAT® SR 30D, EUDRAGIT® NE 30D, and EUDRAGIT® NM 30D (RL/RS:NE) of between 0:100 and 100:0. In certain embodiments, the ammonium salts of copolymers and the neutral copolymers are present in a ratio (ammonium salt copolymers:neutral copolymers) of between 0.5:99.5 to 99.5:0.5, including, but not limited to: 1:99, 2:98, 3:97, 4:96, 5:95, 6:94, 7:93, 8:92, 9:91, 10:90, 11:89, 12:88, 13:87, 14:86, 15:85, 16:84, 17:83, 18:82, 19:81, 20:80, 21:79, 22:78, 23:27, 24:26, 25:75, 26:74, 27:73, 28:72, 29:71, 30:70, 31:69, 32:68, 33:67, 34:66, 35:65, 36:64, 37:63, 38:62, 39:61, 40:60, 50:50, 60:40, 70:30, 80:20, 90:10, 95:5, or any intermediate values thereof. In certain embodiments, the permeable elastic membrane comprises at least one of EUDRAGIT® RL PO and/or EUDRAGIT® RS PO (i.e., solutions of ammonium salts of copolymers). In certain embodiments, the permeable elastic membrane is formed over the core by coating the core with a solution of EUDRAGIT® RL PO and/or EUDRAGIT® RS PO, a plasticizer, and talc.

In certain embodiments, examples of insoluble permeable components of the permeable elastic membrane include, but are not limited to, polymethacrylates (e.g., copolymers of ethyl acrylate, methyl methacrylate, and methacrylic acid ester with quaternary ammonium groups (e.g., EUDRAGIT® RL 30D or EUDRAGIT® RS 30D, EUDRAGIT® RS PO, EUDRAGIT® RL PO)); cellulose acetate phthalate; ethyl cellulose; and hypromellose acetate succinate.

In certain embodiments, examples of insoluble components of the permeable elastic membrane that provide elasticity to the membrane include, but are not limited to, polymethacrylates, e.g., copolymers of ethyl acrylate and methyl methacrylate (e.g., EUDRAGIT® NE 30D, EUDRAGIT® NM 30D), polyvinyl acetates (e.g., KOLLICOAT® SR 30D), thermoplastic polyurethanes, ethylene-vinyl acetate, and polydimethyl siloxane.

In certain embodiments, a pore former can be a water-soluble polymer including, but not limited to, polyvinyl alcohol, polyvinyl pyrrolidone, EUDRAGIT® E PO, hypromellose (HPMC), hydroxypropyl cellulose, methylcellulose, sodium alginate, and polyvinyl alcohol-polyethylene glycol graft polymer. In certain embodiments, a pore former can be a water-soluble organic molecule/surfactant including, but not limited to, citric acid, sodium citrate, tartaric acid, fumaric acid, mannitol, sucrose, fructose, lactose, polyethylene glycol 400, propylene glycol, dextran, glycerin, polysorbate 80, span, vitamin E TPGS, pluronic, gelucire, labrasol, and cyclodextrin. In certain embodiments, a pore former can be an inorganic molecule including, but not limited to, titanium dioxide, potassium chloride, potassium acetate, calcium carbonate, dicalcium phosphate, sodium chloride, sodium bicarbonate, sodium carbonate, magnesium oxide, magnesium sulphate, ammonium sulfide, ammonium chloride, sodium phosphate monobasic and dibasic, talc, and salts of alkali and alkaline earth metals.

In certain embodiments, the permeable elastic membrane comprises a homogeneous dispersion of EUDRAGIT® RL 30D and EUDRAGIT® NE 30D. In certain embodiments, the permeable elastic membrane comprises a homogeneous dispersion of EUDRAGIT® RL 30D and KOLLICOAT® SR 30D. In certain embodiments, the permeable elastic membrane comprises a solution of EUDRAGIT® RL PO and/or EUDRAGIT® RS PO. In certain embodiments, the homogeneous dispersion is formed by mixing EUDRAGIT® RL 30D and EUDRAGIT NE 30D, or EUDRAGIT® RL 30D and KOLLICOAT® SR 30D, in presence of a surfactant and a water soluble polymer, e.g., polyvinyl pyrrolidone. In certain embodiments, the homogeneous dispersion is formed by mixing EUDRAGIT® RL 30D, EUDRAGIT NE 30D, and polyvinyl pyrrolidone, or EUDRAGIT® RL 30D, KOLLICOAT® SR 30D, and polyvinyl pyrrolidone, in a pH-controlled environment, e.g., at a pH of between 2 and 7. In certain embodiments, the homogeneous dispersion is formed at a pH of about 2, about 3, about 4, about 5, about 6, about 7, or any intermediate pH value thereof. In certain embodiments, the homogeneous dispersion is formed by mixing EUDRAGIT® RL 30D and EUDRAGIT NE 30D, or EUDRAGIT® RL 30D and KOLLICOAT® SR 30D, in the absence of a surfactant and/or a water soluble polymer, e.g., polyvinyl pyrrolidone. In certain embodiments, the tablet core is coated with a solution of EUDRAGIT® RL PO and/or EUDRAGIT® RS PO.

In certain embodiments, strength of the membrane depends upon compatibility/homogeneity of the water insoluble polymers present in the coating solution/dispersion. In certain embodiments, compatibility of water insoluble polymers present in the coating dispersion is improved in the presence of a surfactant. In certain embodiments, compatibility of water insoluble polymers present in the coating dispersion is improved by forming the dispersion in an acidic pH of about 2. In certain embodiments, the coating dispersion does not include any neutral polymer to improve mechanical strength of the membrane. In certain embodiments, the coating dispersion includes at least one of EUDRAGIT® RL PO and EUDRAGIT® RS PO (collectively "solutions of ammonium salts of copolymers") to improve permeability and at least one plasticizer to improve mechanical strength (tensile strength).

Immediate Release Layers

In accordance with another embodiment of the disclosure, a degradable gastroretentive dosage form for the sustained release of an active agent can be combined with one or more immediate release layers covering the permeable elastic membrane and comprising the active agent and a polymer and, optionally, other excipients known in the art, that provides for the immediate release of the active agent to form a gastroretentive dosage form for combined immediate release and sustained release of the active agent. Optionally, an additional layer, e.g., an overcoat, covering the outer permeable elastic membrane, comprising a powder or a film that prevents adherence of the outer membranes to itself, can be included.

Examples of soluble film-forming polymers that can be used in the immediate release layer include, but are not limited to, soluble cellulose derivatives, e.g., methyl cellulose; hydroxypropyl cellulose; hydroxyethyl cellulose; hypromellose; various grades of povidone; polyvinyl alcohol and its derivatives, e.g., KOLLICOAT IR; soluble gums; and others. The films can further comprise anti-oxidants, surface-active agents, plasticizers and humectants, such as PEGs, various grades of polysorbates, and sodium lauryl sulfate.

Seal Coat and Over Coat

In certain embodiments, the gastroretentive dosage form of the disclosure further comprises a seal coat between the matrix core and the permeable elastic membrane, and an additional seal coat between the permeable elastic membrane and any immediate release layer. In certain embodiments, the gastroretentive dosage form of the disclosure further comprises a seal coat over the immediate release coat and an over coat over the seal coat. In certain embodiments, the over coat is the outermost coat. In certain embodiments, the seal coat between the matrix core and the permeable elastic membrane, between the permeable elastic membrane and the immediate release layer, and between the immediate release layer and the over coat comprises a pH-independent water-soluble polymer comprising hypromellose, hydroxypropyl cellulose, or a polyvinyl acetate-based polymer. In certain embodiments, the seal coat comprises a polyvinyl acetate-based polymer. In certain embodiments, the overcoat comprises a polyvinyl acetate-based polymer.

Additional Excipients

The disclosed dosage forms can contain one or more additional excipients.

Binders (also sometimes called adhesives) are added to ensure that tablets can be formed with the required mechanical strength. Examples of binders that can be used in the formulation include, but are not limited to, povidone K 90, hypromellose, starch, acacia, gellan gum, low viscosity hydroxypropyl cellulose, methylcellulose, sodium methylcellulose, polyvinyl alcohol, polyvinyl acetates (e.g., KOLLICOAT® SR), polyethylene oxide (e.g., POLYOX®), polyethylene glycol, alginates, and pegylated polyvinyl alcohol. In certain embodiments, binder is hydroxypropyl cellulose.

Diluents or fillers are added to increase the bulk weight of the blend resulting in a practical size suitable for compression. The ideal diluent or filler should fulfill a series of requirements, such as being chemically inert, non-hygroscopic, and biocompatible; possessing appropriate biopharmaceutical properties (e.g., water-soluble or hydrophilic), technical properties (e.g., compactability and sufficient dilution capacity); having an acceptable taste; and preferably being inexpensive. As a single substance is unlikely to meet all these requirements, different substances have gained use as diluents or fillers in tablets.

Apart from sugars, perhaps the most widely used fillers are celluloses in powder forms of different types. Celluloses are biocompatible, chemically inert, and have good tablet forming and disintegrating properties. They are therefore used also as dry binders and disintegrants in tablets. They are compatible with many drugs but, owing to their hygroscopicity, they can be incompatible with drugs prone to hydrolyse in the solid state. The most common type of cellulose powder used in tablet formulation is microcrystalline cellulose. Other important examples of diluents or fillers are dibasic and tribasic calcium phosphate, which are insoluble in water and nonhygroscopic, but are hydrophilic, i.e., easily wetted by water.

In certain embodiments, examples of diluents/compression and bulking agents used in accordance with the present disclosure include, but are not limited to, dicalcium phosphate, mannitol, alginic acid, microcrystalline cellulose, and silicified microcrystalline cellulose. In certain embodiments, the bulking agent or diluent includes mannitol and microcrystalline cellulose.

In certain embodiments, examples of binders that provide structure to the dosage form and trap the in situ-produced gas include, but are not limited to, starch, xanthan gum, povidone, hypromellose, hypromellose acetate succinate, and hydroxypropyl cellulose.

Forms

As an additional method of delivering the immediate release of the drug, a coating can be applied to the capsule comprising the drug. Upon entry into the stomach, the coating will immediately allow release of the drug and enhance the release profile of the drug. Methods for applying coatings to a capsule are well known to those of skill in the art.

The formulations of this disclosure can assume the form of particles, tablets, or particles retained in capsules. In certain embodiments, a formulation can consist of particles consolidated into a packed mass for ingestion, even though the packed mass will separate into individual particles after ingestion. Conventional methods can be used for consolidating the particles in this manner. For example, the particles can be placed in gelatin capsules known in the art as "hard-filled" capsules and "soft-elastic" capsules. The compositions of these capsules and procedures for filling them are known among those skilled in drug formulations and manufacture. The encapsulating material should be highly soluble so that the particles are freed and rapidly dispersed in the stomach after the capsule is ingested. The particles can also be consolidated into a tablet.

6.3 Features of the Dosage Form

Floating gastroretentive dosage forms disclosed herein are not only designed with a control on the release rate of the drug (temporal control) but also with a control on the location of the drug delivery (spatial control). Spatial control for delivery of a drug involves increasing gastric retention time by using a composition containing highly swellable polymers in admixture with a gas-generating agent(s) to form systems that are large enough in size to prevent their passage through the pyloric sphincter, as well as capable of floating on gastric fluids. The systems disclosed herein contain swellable polymers that can rapidly float on gastric fluids because the gas generated and entrapped within the system decreases the density. Further swelling of the floating system to a size that prevents its passage through the pyloric sphincter is an important factor in gastric retention of the system. Floating drug delivery systems not exhibiting swelling (e.g., having a size less than about 5-7 mm) show delayed gastric emptying in fed conditions but can still be emptied from the stomach because their size is smaller than the pyloric sphincter; this can be more likely if the patient is in the supine position. It has been reported that dosage forms with a size of approximately 12-18 mm diameter in their expanded state are generally excluded from passage through the pyloric sphincter (see, e.g., U.S. Patent Application Publication No. 2010/0305208). The systems disclosed herein are capable of retaining this size in the gastric fluids for long periods under hydrodynamic conditions created by gastric motility (i.e., shear effect). Thus, the combination of flotation, a rapid increase in size to prevent its passage through the pyloric sphincter, and retaining the expanded size under hydrodynamic conditions of the stomach in fed and fasted states, results in increased gastric retention of the systems disclosed herein.

It is an object of the present disclosure to provide modified release or combined immediate release and modified release floating gastroretentive dosage forms, with high or low drug loading capacity, containing water soluble drugs, e.g. highly soluble and moderately soluble drugs, that require targeted drug release in the proximal GI tract for maximum therapeutic benefit. The present disclosure provides rapidly expanding gastroretentive dosage forms comprising a permeable elastic membrane with high initial elasticity and tensile strength for controlled drug release, a continuously swelling hydrophilic polymer (e.g., swelling agent) in the tablet core to support the swollen membrane and assist the membrane in providing modified release of the drug, and a gas-generating agent; these features ensure the emptying of the dosage form from the stomach after drug release is complete. It is an object of the disclosure to provide a gastroretentive dosage form that regulates matrix swelling and membrane brittleness as a function of time to enable the gastroretentive dosage form to lose membrane integrity and/or disintegrate at the end of drug release, thereby facilitating the emptying of the gastroretentive dosage form from the stomach. Further, it is an object of the disclosure to provide a gastroretentive dosage form with reduced floating lag time to enable the dosage form to float rapidly.

Figure 3:
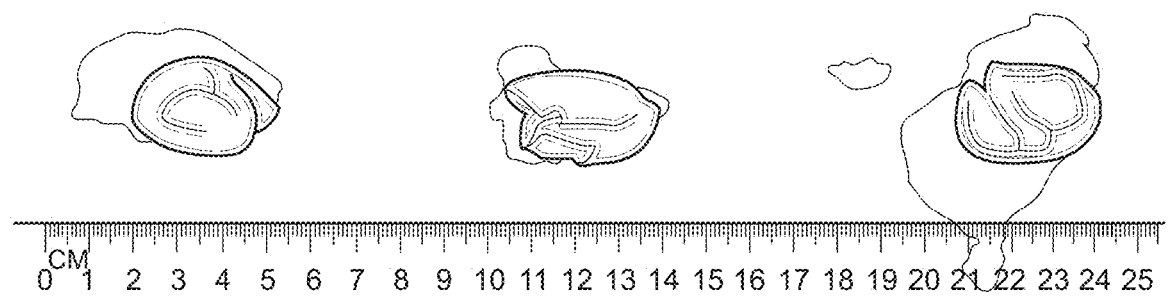
FIG. 3 shows empty shells of tablets of Tablets 2, 3, and 4 after the drug has been released.

With reference to FIG. 3, for the purpose of illustration and not limitation, there is provided a photograph of exemplary empty shells after the drug has been released.

In some embodiments, the present disclosure addresses several of the needs in the art for modified release formulations that provide sustained release for prolonged periods, and/or combined immediate release and sustained release for prolonged periods, of drugs with a NAW in the GI tract, or with other rationales for a gastroretentive administration, by providing gastroretentive dosage forms (of any drug-loading capacity) that provide effective release of the drug for prolonged periods.

In certain embodiments, the gastroretentive dosage forms expand faster due to an initial gas-assisted rapid expansion of the permeable elastic membrane surrounding the core and simultaneous swelling of the core by imbibition of water, wherein the rate of expansion is faster than the rate of swelling. In certain embodiments, dosage forms of the disclosure provide controlled sustained release due to the presence of an opening/orifice running through the membrane and tablet core.

In certain embodiments, the gastroretentive oral dosage form includes a rapidly expanding membrane with high tensile strength and elasticity that expands the dosage form in about 30 minutes (or less) to a size that prevents its passage through the pyloric sphincter, and a hydrophilic matrix core, surrounded by the membrane, that swells with imbibition and absorption of fluid and assists the membrane in providing a sustained release of the drug. In certain embodiments, the membrane provides a sustained release of the drug for about one to twenty-four hours, e.g., about eight to sixteen hours.

As noted above, in certain embodiments, the matrix core comprises gas-generating agents, e.g., carbonate and bicarbonate salts, that generate $CO_2$ in presence of acidic gastric fluid. In certain embodiments, the matrix core further comprises organic and/or inorganic acids that react with carbonate salts in an aqueous environment, e.g., at neutral pH or at a weakly acidic pH, and generate $CO_2$ gas. In certain embodiments, the membrane is highly elastic/flexible due to the presence of at least one plasticizer and expands rapidly with an outward pressure on the membrane from the generated $CO_2$ gas. In certain embodiments, the dosage form of the disclosure exhibits at least about 200% volume gain in about 30 minutes, at least about 400% volume gain in about 45 minutes, and at least about 550% volume gain in about 60 minutes. In certain embodiments, the rate of swelling of the matrix core is less than the rate of expansion of the membrane, such that the matrix core expands unrestricted dimensionally. In certain embodiments, the membrane expansion is responsible for an initial rapid expansion of the dosage form and the swellable matrix within the membrane supports the expanded membrane.

Figure 2A:
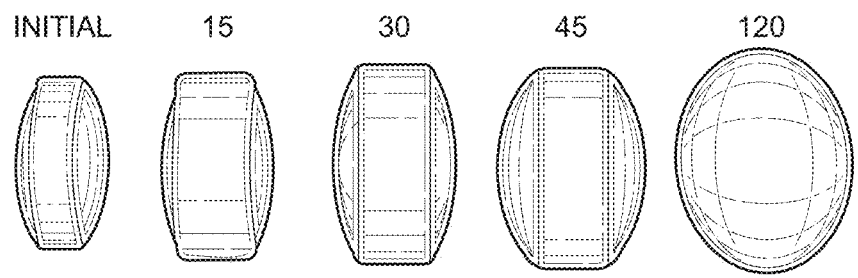
FIGS. 2A-2B show the swelling of dosage forms according to certain embodiments as a function of time (FIG. 2A) and as a function of the type of gas-generating agent (FIG. 2B).

With reference to FIG. 2A for the purpose of illustration and not limitation, there is provided a photograph of the swelling of dosage forms according to certain embodiments as a function of time. FIG. 2A shows the progressive swelling of an exemplary dosage form at time 0, and after 15, 30, 45 and 120 minutes.

Figure 2B:
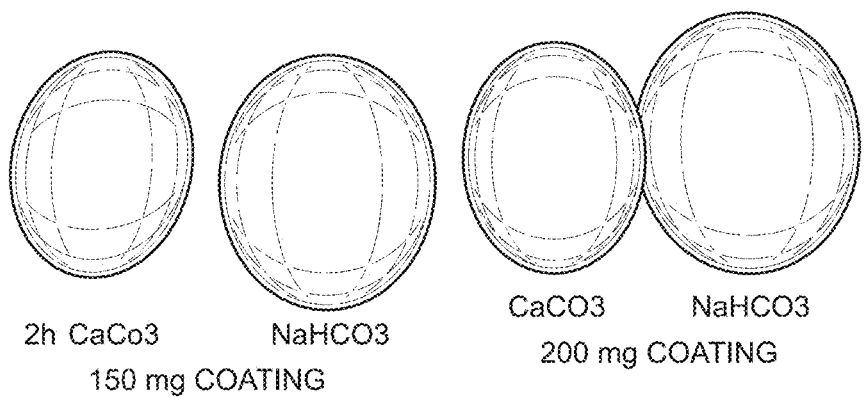

With reference to FIG. 2B for the purpose of illustration and not limitation, there is provided a photograph of the swelling of dosage forms according to certain embodiments as a function of the type of gas-generating agent. FIG. 2B compares exemplary dosage forms after 2 hours' swelling for 150 mg and 200 mg coatings for calcium carbonate and sodium bicarbonate.

In certain embodiments, the expanded dosage form shrinks back to about 200% volume gain in about 4 hours or less, about 150% volume gain in about 8 hours or less, and about 100% volume gain in about 14 hours or less. In certain embodiments, the dosage form shrinks due to diffusion of $CO_2$ through the membrane into the surrounding environment. In certain embodiments, the hydrophilic matrix core swells to a size that can support the expanded permeable elastic membrane. In certain embodiments, the permeable elastic membrane keeps the core intact in a swollen condition for a sufficient period of time and provides the desired characteristics of drug release.

The gastroretentive oral floating dosage form of the disclosure markedly improves absorption and bioavailability of suitable active agents and, in particular, ameliorates the absorption and bioavailability of drugs having an NAW in the proximal GI tract, due to its ability to withstand peristalsis and mechanical contractility of the stomach (shear, or shear effect), and consequently releases the drug in a sustained manner in the vicinity of its absorption site(s) and without premature transit into nonabsorbing regions of the GI tract.

In certain embodiments, the gastroretentive dosage form of the disclosure provides gastric retention of an active agent for up to 1, 2, 3, 4, 5, 6, 7, 8, 9, 10, 11, 12, 13, 14, 15, 16, 17, 18, 19, 20, 21, 22, 23, 24, or more hours. In certain embodiments, the gastroretentive dosage form of the disclosure provides gastric retention of an active agent for between, e.g., 1-24, 10-20, 12-18, and 14-16 hours. In certain embodiments, the gastroretentive dosage form of the disclosure provides gastric retention of an active agent for about 12 hours. In addition, administration of these formulations to a mammal can improve the pharmacokinetic and pharmacodynamic properties of an active agent(s) having a NAW. Furthermore, as the drug diffuses out of the tablet core and the polymeric excipients in the core continue to swell, the plasticizer leaches out and the permeable elastic membrane loses its integrity and starts to break, thereby allowing remnants of the drug formulation and the remaining contents to be expelled from the stomach at an appropriate time, e.g., after a prolonged period of drug release.

In certain embodiments, the presence of a water-soluble cellulose ether polymer, a gas-generating agent, and an acid in the matrix core, and a water-insoluble permeable elastic membrane (applied over the seal coat) comprising a homogeneous dispersion of EUDRAGIT® RL PO, and at least one nonionic water-soluble polymer as pore former, formed in a pH-adjusted environment or in the presence of a surfactant, provides rapidly expanding controlled release gastroretentive dosage form with desired characteristics for drug release, hydrodynamic balance, and mechanical strength to withstand pH variations and shear effect in the stomach during fed and fasted conditions.

In certain embodiments, desired characteristics for drug release, hydrodynamic balance, and mechanical strength to withstand pH variations and shear effect in the stomach during fed and fasted conditions are achieved in the absence of a pore former. In certain embodiments, the water-insoluble permeable elastic membrane comprises EUDRAGIT® RL 30D and/or EUDRAGIT® NE 30D. In certain embodiments, the water insoluble permeable elastic membrane comprises EUDRAGIT® RL PO and/or EUDRAGIT® RS PO.

In certain embodiments, the oral floating gastroretentive dosage forms are stable, and provide efficient delivery of various drugs in the GI tract due to the presence of a water-soluble polymer, e.g., hypromellose, that swells via imbibition of water from gastric fluid to (1) increase the size of the dosage form to promote gastric retention, (2) partially control the release of drug by entrapping the drug in the swollen polymer, (3) support the membrane and maintain the integrity of the tablet in a swollen state with a seal coat and/or by forming a layer (e.g., a hydrogel layer) beginning at the periphery of the matrix core, and (4) entrap generated gas (e.g., $CO_2$) to provide buoyancy. In certain embodiments, an initial rapid expansion of the permeable elastic membrane provides room for swelling of hypromellose. In certain embodiments, the increase in the size of the dosage form is due to rapid expansion of the membrane and gradual swelling of the matrix core.

In certain embodiments, the gastroretentive dosage form comprises: i) a modified release matrix core comprising an active agent, a superdisintegrant, a water-soluble polymer that swells via imbibition of water from gastric fluid, a gas-generating agent, and, optionally, an acid, and ii) a sustained release water-insoluble, permeable elastic membrane over the matrix core comprising at least one copolymer based on ethyl acrylate and methyl methacrylate, and optionally, a polyvinyl acetate polymer. The dosage form, independent of the stomach pH, swells rapidly to a size that prevents its passage through the pyloric sphincter, and the membrane maintains the integrity of the system in a swollen state for a prolonged period of time under hydrodynamic conditions created by gastric motility (shear effect) and pH variations.

In certain embodiments, the gastroretentive dosage form of the disclosure expands within 10-15 minutes, reaching a size that prevents its passage through the pyloric sphincter in 30 minutes or less. In certain embodiments, the gastroretentive dosage form of the disclosure shows up to a three-fold increase in volume (i.e., a 200% volume gain) over a period of about 30 minutes.

In certain embodiments, the gastroretentive dosage form of the disclosure expands within 30 minutes to a size that prevents its passage through the pyloric sphincter, and exhibits a floating lag time of less than 20 minutes, e.g., less than 19 minutes, less than 18 minutes, less than 17 minutes, less than 16 minutes, less than 15 minutes, less than 14 minutes, less than 13 minutes, less than 12 minutes, less than 11 minutes, less than 10 minutes, or less than 9 minutes.

In certain embodiments, the gastroretentive dosage form of the disclosure exhibits a breaking strength of greater than about 15 N.

In certain embodiments, the gastroretentive dosage form of the disclosure provides a controlled sustained release of the active agent for a period of about 8-16 hours, e.g., about 12 hours, under fed and fasted conditions. In certain embodiments, the gastroretentive dosage form contains levodopa/carbidopa as the active agents, and provides a sustained release of carbidopa/levodopa in 0.1N/0.01N HCl (similar to fasted conditions) and in an acetate buffer (pH 4.5; similar to fed conditions), using a rotating bottle apparatus at different hydrodynamic conditions (e.g., 15 rpm and 30 rpm) at 37° C.

In certain embodiments, the dosage form provides a sustained release, for at least about 12 hours, of carbidopa and levodopa in 200 ml of pH 4.5 acetate buffer, measured using biodisk/reciprocating cylinder method at 25 dpm.

In certain embodiments, the dosage form provides a sustained release of carbidopa and levodopa, for at least 12 hours, in 900 ml of pH 4.5 acetate buffer, measured using custom basket method at 100 rpm.

In certain embodiments, the gastroretentive dosage form contains pyridostigmine bromide as the active agent, and provides a sustained release, for at least about 12 hours, of pyridostigmine bromide in 50 mM pH 4.5 acetate buffer, measured using USP 1 custom basket method at 100 rpm.

The present disclosure provides sustained release, or combined immediate release and sustained release floating gastroretentive drug formulations, with high, medium, or low drug loading capacity, containing drugs that require targeted drug release in the proximal GI tract for maximum therapeutic benefit. The present disclosure provides rapidly expanding gastroretentive dosage forms comprising a permeable membrane with high elasticity and tensile strength for sustained drug release, and a continuously swelling hydrophilic polymer, with a floating lag time of less than about 15 minutes, in the tablet core to provide rapid floatation of the dosage form, prevent dose dumping and ensure the emptying of the dosage form after drug release is complete.

Figure 4:
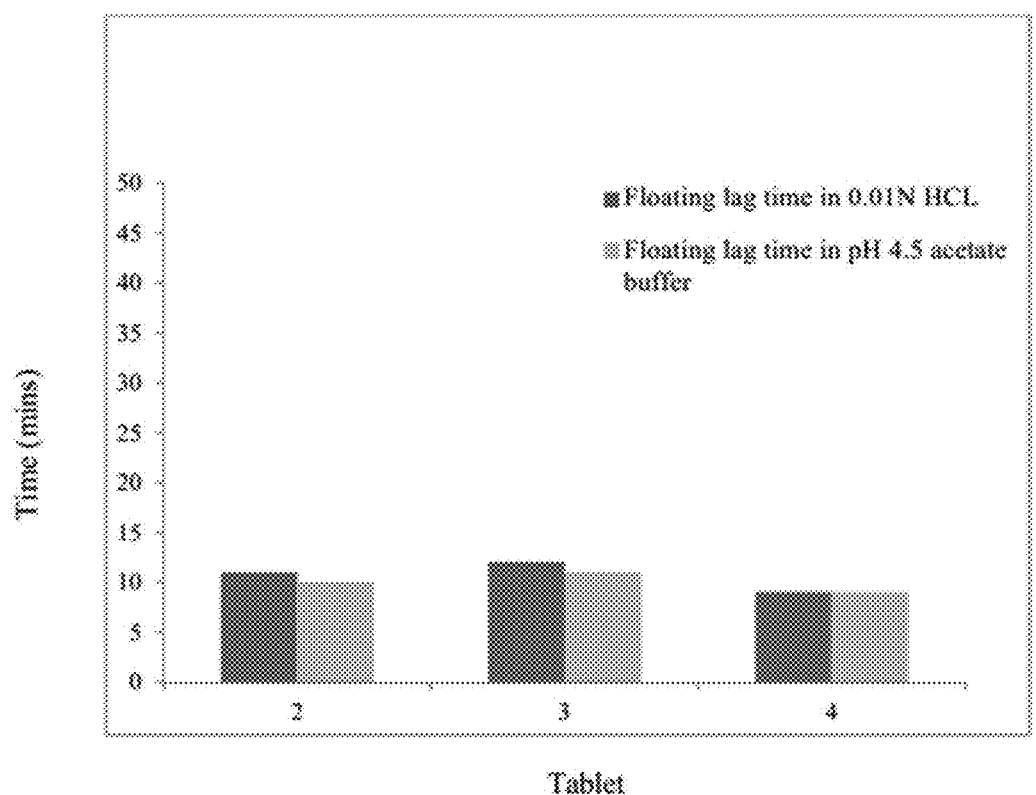
FIG. 4 shows floating lag time of Tablets 2, 3, and 4, measured in a rotating bottle, at 15 rpm, in 200 ml of 0.01N HCl, and of pH 4.5 acetate buffer.

The gastroretentive dosage forms of the disclosure can conveniently release active agents in a sustained release profile, or in a combined immediate and sustained release profile, over a prolonged period, while maintaining high drug bioavailability for an extended period of time. Because gastric retention depends primarily on swelling and floating mechanisms, the swelling behavior was evaluated in terms of gravimetric swelling (water uptake) and volumetric swelling (size increase). FIGS. 9, 10, and 20 show swelling kinetics (volumetric and gravimetric) of test formulations. As the entrapment of in situ-generated carbon dioxide produced by the reaction between sodium bicarbonate and/or calcium carbonate with the acid and/or the acidic gastric media, floating lag time was also measured (FIG. 4). In addition, a test of a tablet's ability to withstand shear forces, offering higher discrimination of the effects of such forces, was also utilized: a rotating bottle method at 15 and 30 rpm (FIGS. 5-8, 11 and 12), and a biodisk/reciprocating cylinder method at 25 dpm (FIGS. 13, 14, 17 and 18). The test procedures to measure these properties are described in the Examples below.

6.4 Active Agents

The gastroretentive dosage forms are particularly beneficial for active agents that have variable transit times through various regions of the GI tract, have narrow absorption window in the regions of GI tract, are susceptible to degradation in alkaline environment, require acidic environment for maximum solubility, and/or are precipitated in alkaline environment. As noted above, gastric retention sustained drug delivery systems of the present disclosure is useful in providing improved drug delivery. Agents that can be used in the gastric retention controlled drug delivery system of the present disclosure include, but are not limited to, the following groups of agents: alcohol abuse preparations, drugs used for Alzheimer's disease, anesthetics, acromegaly agents, analgesics, anti-asthmatics, anticancer agents, anticoagulant and antithrombotic agents, anticonvulsants, antidiabetic agents, antiemetics, antiglaucoma agents, antihistamines, anti-infective agents, anti-Parkinson's agents, antiplatelet agents, antirheumatic agents, antispasmodics and anticholinergic agents, antitussives, carbonic anhydrase inhibitors, cardiovascular agents, cholinesterase inhibitors, treatment of CNS disorders, CNS stimulants, contraceptives, cystic fibrosis management, dopamine receptor agonists, endometriosis management, erectile dysfunction therapy, fertility agents, gastrointestinal agents, immunomodulators and immunosuppressives, memory enhancers, migraine preparations, muscle relaxants, nucleoside analogues, osteoporosis management, parasympathomimetics, prostaglandins, psychotherapeutic agents, sedatives, hypnotics and tranquilizers, drugs used for skin ailments, steroids, and hormones.

In certain embodiments, the gastroretentive dosage form of the disclosure can be used for all classes of drugs/active agents that can take advantage of the gastroretentive dosage forms for improved local or systemic delivery. Examples of such drugs include drugs for local effect in stomach, weakly basic drugs, drugs with reduced bioavailability, drugs with higher stability in gastric region, drugs with NAW, and drugs interfering with normal gut flora in the colon.

Examples of drugs providing local effect in the stomach include, but are not limited to, Hi receptor agonists, antacids, agents for treatment of *Helicobacter pylori* (*H. pylori*), gastritis, gastric ulcers/cancer including misoprostal, amoxicillin, tetracycline, metronidazole, rebamipide, sulfasalazine, and their salts. In addition, active agents that act locally are, for example, drugs for the treatment of local infections, or drugs for the treatment of various GI diseases and symptoms (e.g., misoprostal for gastric ulcers), or drugs for the treatment of metabolic disorders, for the treatment of local cancers or for the treatment of cancer-related diseases. More specifically, the agents relevant in this aspect are those that must be administered in the inflamed bowel, as occurs during inflammatory bowel diseases, such as metronidazole, vancomycin, budesonide, mesalamine, sulfasalazine, and others, whose efficacy is impaired by unusually rapid emptying by the inflamed tissue. These materials can be poorly absorbed systemically, such as vancomycin, or could be incorporated into a targeted delivery system, such as for budesonide.

Weakly basic drugs include, but are not limited to, acetaminophen, rofecoxib, celecoxib, morphine, codeine, oxycodone, hydrocodone, diamorphine, pethidine, tramadol, buprenorphine, prazosin, nifedipine, lercanidipine, amlodipine besylate, trimazosin, doxazosin, hydroxyzine hydrochloride, lorazepam, buspirone hydrochloride, pazepam, chlordiazepoxide, meprobamate, oxazepam, trifluoperazine hydrochloride, clorazepate dipotassium, diazepam, abciximab, eptifibatide, tirofiban, lamifiban, clopidogrel, ticlopidine, dicumarol, heparin, warfarin, phenobarbital, methylphenobarbital, clobazam, clonazepam, clorezepate, diazepam, midazolam, lorazepam, felbamate, carbamezepine, oxcarbezepine, vigabatrin, progabide, tiagabine, topiramate, gabapentin, pregabalin, ethotoin, phenytoin, mephenytoin, fosphenytoin, paramethadione, trimethadione, ethadione, beclamide, primidone, brivaracetam, levetiracetam, seletracetam, ethosuximide, phensuximide, mesuximide, acetazolamide, sulthiame, methazolamide, zonisamide, lamotrigine, pheneturide, phenacemide, valpromide, valnoctamide, repaglinide, nateglinide, metformin, phenformin, rosiglitazone, pioglitazone, troglitazone, miglitol, acarbose, exanatide, vildagliptin, sitagliptin, tolbutamide, acetohexamide, tolazamide, glyburide, glimepiride, gliclazide, glipizide, chlorpropamide, pseudoephedrine, phenylephrine, oxymetazoline, mepyramine, antazoline, diphenhydramine, carbinoxamine, doxylamine, clemastine, dimenhydrinate, pheniramine, chlorpheniramine, dexchlorpheniramine, brompheniramine, tripolidine, cyclizine, chlorcyclizine, hydroxyzine, meclizine, promethazine, trimeprazine, cyproheptadine, azatadine, ketotifen, dextromethorphan, noscapine, ethyl morphine, codeine, chlorambucil, lomustine, tubulazole, echinomycin, betamethasone, prednisolone, aspirin, piroxicam, valdecoxib, carprofen, celecoxib, flurbiprofen, (+)-N-{4-[3-(4-fluorophenoxy)phenoxy]-2-cyclopenten-1-yl}-N-hyroxyurea, timolol, nadolol, dextromethorphan, noscapine, ethyl morphine, theobromine, codeine, actinomycin, dactinomycin, doxorubicin, daunorubicin, epirurubicin, bleomycin, plicamycin, mitomycin, alprenolol, carteolol, levobunolol, mepindolol, metipranolol, nadolol, oxprenolol, penbutolol, pindolol, propranolol, sotalol, timolol, acebutolol, atenolol, betaxolol, bisoprolol, esmolol, metoprolol, nebivolol, carvedilol, celiprolol, labetalol, butaxemine, adalimumab, azathioprine, chloroquine, hydroxychloroquine, D-penicillamine, etanercept, sodium aurothiomalate, auranofin, infliximab, leflunomide, minocycline, sulfasalazine, hydrocortisone, prednisone, prednisolone, methylprednisolone, dexamethasone, betamethasone, triamcinolone, beclomethasone, aldosterone, acetaminophen, amoxiprin, benorilate, diflunisal, faislamine, diclofenac, aceclofenac, acemetacin, bromfenac, etodolac, indomethacin, nabumetone, sulindac, tolmetin, carprofen, ketorolac, mefenamic acid, matamizole, oxyphenbutazone, sulfinprazone, piroxicam, lomoxicam, meloxicam, tenoxicam, celecoxib, etoricoxib, lumiricoxib, parecoxib, rofecoxib, valdecoxib, numesulide, iloperidone, ziprasidone, olanzepine, thiothixene hydrochloride, fluspirilene, risperidone, penfluridole, ampakine, atorvastatin calcium, cerivastatin, fluvastatin, lovastatin, mevastatin, pitavastatin, pravastatin, rosuvastatin, simvastatin, dexadrine, dexfenfluramine, fenfluramine, phentermine, orlistat, acarbose, rimonabant, sildenafil citrate, carbenicillin indanylsodium, bacampicillin hydrochloride, troleandomycin, doxycyline hyclate, ampicillin, penicillin G, oxytetracycline, minocycline, erythromycin, spiramycin, acyclovir, nelfinavir, virazole, benzalkonium chloride, chlorhexidine, econazole, terconazole, fluconazole, voriconazole, metronidazole, thiabendazole, oxiendazole, morantel, cotrimoxazole, alfaxalone, etomidate, levodopa, bromocriptine, pramipexole, ropinirole, pergolide, selegiline, trihexyphenidyl, benztropine mesylate, procyclidine, biperiden, ethopropazine, diphenhydramine, dolphenadrine, amantadine, donepezil, rivastigmine, galantamine, tacrine, minocycline, rifampin, erythromycin, nafcillin, cefazolin, imipenem, aztreonam, gentamicin, sulfamethoxazole, vancomycin, ciprofloxacin, trimethoprim, metronidazole, clindamycin, telcoplanin, mupirocin, ofloxacin, lomefloxacin, norfloxacin, nalidixic acid, sparfloxacin, pefloxacin, amifloxacin, enoxacin, fleroxacin, ternafloxacin, tosufloxacin, clinafloxacin, sulbactam, clavulanic acid, amphotericin B, fluconazole, itraconazole, ketoconazole, nystatin, isocarboxazid, phenelzine, tranylcypromine, azidovudine (AZT), didanosine (dideoxyinosine, ddI), d4T, zalcitabine (dideoxycytosine, ddC), nevirapine, lamivudine (epivir, 3TC), saquinavir, ritonavir, indinavir delavirdine, [R—(R*S*)]-5-chloro-N-[2-hydroxy-3-{methoxymethylamino}-3-oxo-1-(phenylmethyl)propyl-1H-indole-2-carboxamide, 5-chloro-1H-indole-2-carboxylic acid [(1S)-benzyl-(2R)-hydroxy-3-((3R,4S)-dihydroxy-pyrrolidin-1-yl-)-3-o-xypropyl]amide, [2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester, [2R,4S]4-[acetyl-(3,5-bis-trifluoromethyl-benzyl)-amino]-2-ethyl-6-trifluoromethyl-3,4-dihydro-2H-quinoline-1-carboxylic acid isopropyl ester, [2R,4S]4-[(3,5-Bis-trifluoromethyl-benzyl)-methoxycarbonyl-amino]-2-eth-yl-6-trifluoromethyl-3,4-dihydro-2H-quinoline-1-carboxylic acid isopropyl ester, caffeine, methylphenidate, cabergoline, pramipexole, dolasetron, granisetron, ondansetron, tropisetron, palonosetron, domperidone, droperidol, dimenhydrinate, haloperidol, chlorpromezine, promethazine, prochlorperizine, metoclopramide, alizapride, loperamide, cisapride, chlorpromazine, thioridazine, prochlorperizine, haloperidol, alprazolam, amitriptyline, bupropion, buspirone, chlordiazepoxide, citalopram, clozapine, diazepam, fluoxetine, fluphenazine, fluvoxamine, hydroxyzine, lorezapam, loxapine, mirtazepine, molindone, nefazodone, nortriptyline, olanzepine, paroxetine, phenelzine, quetiapine, risperidone, sertraline, thiothixene, tranylcypromine, trazodone, venlafaxine, ziprasidone, hydromorphone, fentanyl, methadone, morphine, oxycodone, oxymorphone, naltrexone, sodium valproate, nitrazepam, phenytoin, famonizatidine, cimetidine, ranitidine, albuterol, montelukast sodium, nicorandil, iloperidone, clonazepam, diazepam, lorazepam, baclofen, carisoprodol, chlorzoxazone, cyclobenzaprine, dantrolene, metaxalone, orphenadrine, pancuronium, tizanidine, dicyclomine, clonidine, gabapentin, and salbutamol.

An example of a drug with reduced bioavailability isacyclovir.

Examples of drugs with greater stability in the gastric region are liothyronine ($T_3$), levothyroxine ($T_4$), $T_3/T_4$ combinations, captopril, ranitidine HCL, metformin, tetracycline, and metronidazole.

Examples of drugs with NAW are aspirin, levodopa, p-aminobenzoic acid, metronidazole, amoxicillin, sulphonamides, quinolones, penicillins, cephalosporins, aminoglycosides, liothyronine ($T_3$), levothyroxine ($T_4$), $T_3/T_4$ combinations, and tetracyclines.

Examples of drugs that interfere with normal gut flora in the colon, e.g., orally active antibiotics such as ampicillin, and amoxycillin.

Each named drug should be understood to include the neutral form of the drug, as well as pharmaceutically acceptable salts, solvates, esters, and prodrugs thereof.

7. EXAMPLES

The detailed description of the present disclosure is further illustrated by the following Examples, which are illustrative only (e.g., focusing here only on levodopa/carbidopa) and are not to be construed as limiting the scope of the disclosure. Variations and equivalents of these Examples will be apparent to those skilled in the art in light of the present disclosure, the drawings, and the claims herein.

Example 1: Levodopa/Carbidopa Tablet Core

Tablet cores were prepared for use in 200/53.7 mg and 300/80.6 mg levodopa/carbidopa dosage forms.

TABLE 1

Formulation of levodopa/carbidopa tablet core (levodopa 200 mg/carbidopa 53.7 mg)

| Ingredients | A (mg) | B (mg) | C (mg) | D (mg) | E (mg) | F (mg) | G (mg) | H (mg) |
|---|---|---|---|---|---|---|---|---|
| Levodopa Granules | | | | | | | | |
| Levodopa | 200.0 | 200.0 | 200.0 | 200.0 | 200.0 | 200.0 | 200.0 | 200.0 |
| Microcrystalline cellulose | 33.3 | 33.3 | 33.3 | 33.3 | 33.3 | 33.3 | 33.3 | 33.3 |
| Mannitol | 66.7 | 66.7 | 66.7 | 66.7 | 66.7 | 66.7 | 66.7 | 66.7 |
| Hydroxypropyl cellulose | 3.3 | 3.3 | 3.3 | 3.3 | 3.3 | 3.3 | 3.3 | 3.3 |
| Total | 303.3 | 303.3 | 303.3 | 303.3 | 303.3 | 303.3 | 303.3 | 303.3 |
| Carbidopa Granules | | | | | | | | |
| Carbidopa monohydrate | 53.7 | 53.7 | 53.7 | 53.7 | 53.7 | 53.7 | 53.7 | 53.7 |
| Microcrystalline cellulose | 13.3 | 13.3 | 13.3 | 13.3 | 13.3 | 13.3 | 13.3 | 13.3 |
| Mannitol | 53.4 | 53.4 | 53.4 | 53.4 | 53.4 | 53.4 | 53.4 | 53.4 |
| Alpha tocopherol | | | | | 0.5 | 0.5 | 0.5 | |
| Magnesium stearate | 6.7 | 6.7 | 6.7 | 6.7 | 7.9 | 7.9 | 7.9 | 6.7 |
| Total | 127.1 | 127.1 | 127.1 | 127.1 | 128.8 | 128.8 | 128.8 | 127.1 |
| Total LD/CD Granules | 430.4 | 430.4 | 430.4 | 430.4 | 432.1 | 432.1 | 432.1 | 430.4 |

TABLE 1-continued

Formulation of levodpa/carbidopa tablet core (levodopa 200 mg/carbidopa 53.7 mg)

| Ingredients | A (mg) | B (mg) | C (mg) | D (mg) | E (mg) | F (mg) | G (mg) | H (mg) |
|---|---|---|---|---|---|---|---|---|
| Extragranular Excipients | | | | | | | | |
| Sodium bicarbonate | 50.0 | 50.0 | 50.0 | 50.0 | 50.0 | 50.0 | 50.0 | 50.0 |
| Calcium Carbonate | 125.0 | 125.0 | 125.0 | 125.0 | 125.0 | 125.0 | 125.0 | 125.0 |
| Crospovidone, XL | 100.0 | 100.0 | 100.0 | 100.0 | 100.0 | 100.0 | 100.0 | 100.0 |
| Mannitol | 184.6 | 184.6 | 184.6 | 184.6 | 185.4 | 185.4 | 185.4 | 184.6 |
| Microcrystalline cellulose | 50.0 | 50.0 | 50.0 | 50.0 | 50.0 | 50.0 | 50.0 | 50.0 |
| Methocel, K15M | 50.0 | — | 25.0 | — | 50 | — | — | — |
| Methocel K4M (or CR) | — | 50.0 | 25.0 | — | — | 50 | — | — |
| Carbopol 974p | — | — | — | 50 | — | — | — | — |
| Sodium alginate | — | — | — | — | — | — | 50.0 | — |
| Magnesium stearate | 10.0 | 10.0 | 10.0 | 10.0 | 7.5 | 7.5 | 7.5 | 10.0 |
| Total weight | 1000.0 | 1000.0 | 1000.0 | 1000.0 | 1000.0 | 1000.0 | 1000.0 | 950.0 |

TABLE 2

Formulation of levodopa/carbidopa tablet core (levodopa 300 mg/carbidopa 80.6 mg)

| Ingredients | I (mg) | J (mg) | K (mg) | L (mg) | M (mg) | N (mg) | O (mg) | P (mg) |
|---|---|---|---|---|---|---|---|---|
| Levodopa | | | | | | | | |
| Levodopa | 300.0 | 300.0 | 300.0 | 300.0 | 300.0 | 300.0 | 300.0 | 300.0 |
| Microcrystalline | 20.0 | 20.0 | 20.0 | 20.0 | 20.0 | 20.0 | 25.0 | 25.0 |
| Crospovidone | 5.0 | 5.0 | 5.0 | 5.0 | 5.0 | 5.0 | 23.0 | 23.0 |
| Hydroxypropyl | 5.0 | 5.0 | 5.0 | 5.0 | 5.0 | 5.0 | 3.0 | 3.0 |
| Mannitol | 30.0 | 30.0 | 30.0 | 30.0 | 30.0 | 30.0 | — | — |
| Total | 360.0 | 360.0 | 360.0 | 360.0 | 360.0 | 360.0 | 351.0- | 351.0 |
| Carbidopa | | | | | | | | |
| Carbidopa | 80.6 | 80.6 | 80.6 | 80.6 | 80.6 | 80.6 | 75.0 | 75.0 |
| Microcrystalline | 30.0 | 30.0 | 30.0 | 30.0 | 29.5 | 29.5 | 20.0 | 20.0 |
| Alpha tocopherol | — | — | — | — | 0.5 | 0.5 | — | — |
| Mannitol | 30.0 | 30.0 | 30.0 | 30.0 | 30.0 | 30.0 | — | — |
| Magnesium stearate | 10.0 | 10.0 | 10.0 | 10.0 | 10.0 | 10.0 | 4.0 | 4.0 |
| Total | 151.0 | 151.0 | 151.0 | 151.0 | 151.0 | 151.0 | 99.0 | 99.0 |
| Total LD/CD | 511.0 | 511.0 | 511.0 | 511.0 | 511.0 | 511.0 | 450.0 | 450.0 |
| Extragranular | | | | | | | | |
| Sodium bicarbonate | 50.0 | 50.0 | 50.0 | 50.0 | 50.0 | 50.0 | — | 100.0 |
| Calcium carbonate | 100.0 | 100.0 | 100.0 | 100.0 | 125.0 | 125.0 | 175.0 | — |
| Crospovidone, XL | 100.0 | 100.0 | 100.0 | 100.0 | 100.0 | 100.0 | 175.0 | 175.0 |
| Mannitol | 154.0 | 154.0 | 154.0 | 154.0 | 154.0 | 154.0 | 120.0 | 195.0 |
| Microcrystalline | 25.0 | 50.0 | 50.0 | 50.0 | 50.0 | 80.0 | 50.0 | 50.0 |
| Methocel, K15M | 25.0 | — | — | — | — | — | — | — |
| Methocel K4M | — | 50.0 | 25.0 | 25.0 | 50.0 | 50.0 | — | — |
| Methocel K100LV | 25.0 | — | 25.0 | — | — | — | — | — |
| Sodium alginate | — | — | — | 25.0 | — | — | — | — |
| Medi-Gel | — | — | — | — | — | 20.0 | — | — |
| Corn Starch | — | — | — | — | — | — | 20.0 | 20.0 |
| Magnesium stearate | 10.0 | 10.0 | 10.0 | 10.0 | 10.0 | 10.0 | 10.0 | 10.0 |
| Total weight | 1000.0 | 1025.0 | 1015.0 | 1015.0 | 1050.0 | 1100.0 | 1000.0 | 1000.0 |

Manufacturing Procedure:
1. Preparing levodopa granules: Levodopa granules were made by high shear wet granulation process. Levodopa, microcrystalline cellulose, mannitol, and hydroxypropyl cellulose were placed in a high shear granulator, and mixed into a uniform powder blend. The powder blend from was wet granulated using water as granulation fluid. Wet granules were dried in a fluid bed dryer and milled using an impact mill to prepare uniform sized levodopa granules.

2. Preparing carbidopa granules: Carbidopa granules were made using either dry granulation or ethanolic granulation process. Carbidopa was blended with microcrystalline cellulose, mannitol, and magnesium stearate in a high shear granulator. The powder blend was granulated with an ethanolic solution of alpha tocopherol. Additional quantity of ethanol was added as needed to achieve uniform granulation. The granules were dried in a forced-air oven at 40° C. or a fluid bed dryer to remove the solvent, and the dried granules were passed through US mesh screen #30. In some embodiments, the powder blend containing carbidopa, microcrystalline cellulose, and mannitol was mixed with magnesium stearate and granulated by a dry granulation process, such as slugging.

3. Mixing with extragranular excipients: Levodopa and carbidopa granules, as obtained from Steps #1 and #2, were blended with extragranular portions of sodium bicarbonate, calcium carbonate, microcrystalline cellulose, mannitol, crospovidone XL, hypromellose (or sodium alginate, or a mixture of hypromellose and sodium alginate), and magnesium stearate. The final blend was compressed into a tablet core using a suitable tablet press.

In an alternative process, levodopa and carbidopa granules obtained from Steps #1 and #2 can be blended with extragranular portions of sodium bicarbonate, calcium carbonate, microcrystalline cellulose, mannitol, crospovidone XL, hypromellose (or sodium alginate, or a mixture of hypromellose and sodium alginate, or a carbomer (CARBOPOL)) and magnesium stearate, and granulated by dry granulation process such as slugging followed by milling. The final granulate blend is then compressed into a tablet core using a suitable tablet press.

Example 2: Levodopa/Carbidopa Tablet Core

Tablet cores were prepared for use in 200/50.0 mg and 175.0/43.75 mg levodopa/carbidopa dosage forms.

TABLE 3

Formulation of levodopa/carbidopa tablet core

| Ingredients | Q (mg) | R (mg) | S (mg) |
|---|---|---|---|
| Intragranular | | | |
| Carbidopa* | 54.00 | 47.25 | 54.00 |
| Levodopa | 200.0 | 175.0 | 200.0 |
| Mannitol | 137.5 | 120.0 | 137.5 |
| Hydroxypropyl cellulose | 8.00 | 7.00 | 8.00 |
| dl-α-tocopherol | 0.500 | 0.44 | 0.500 |
| Succinic acid | 50.00 | 43.75 | 50.00 |
| Ethyl alcohol 200 proof, absolute | — | — | — |
| Extragranular | | | |
| Sodium bicarbonate | 50.00 | 43.75 | 50.00 |
| Calcium carbonate | 125.0 | 109.4 | 50.00 |
| Crospovidone, NF (Polyplasdone XL) | 100.0 | 87.50 | 100.0 |
| Mannitol | 163.0 | 141.4 | 238.0 |
| Hypromellose | 50.00 | 43.75 | 50.00 |
| Magnesium stearate | 8.00 | 7.00 | 8.00 |
| Colloidal silicon dioxide (CABOSIL) | 4.00 | 3.5 | 4.00 |
| Total | 950.0 | 830.0 | 950.0 |

*54.0 mg carbidopa monohydrate/tablet is equivalent to 50.0 mg carbidopa/tablet.
*47.25 mg carbidopa monohydrate/tablet is equivalent to 43.75 mg carbidopa/tablet.

Manufacturing Procedure:
1. Preparing Levodopa/carbidopa co-granules: Levodopa/carbidopa co-granules were made by high shear wet granulation process. Levodopa, carbidopa, mannitol, hydroxypropyl cellulose, and succinic acid were placed in a high shear granulator and mixed into a uniform powder blend. The powder blend was wet granulated using Ethanol and vitamin-E mixture as granulation fluid. The resulting wet granules were dried in a fluid bed dryer and milled using an impact mill to prepare uniform sized levodopa/granules.
2. Mixing with extragranular excipients: The levodopa/carbidopa co-granules from Step #1 were blended with sodium bicarbonate, calcium carbonate, crospovidone XL, mannitol, hypromellose, colloidal silicon dioxide, and magnesium stearate. The final blend was compressed into a tablet core using a suitable tablet press.

In an alternative process, levodopa and carbidopa cogranules obtained from Step #1 can be blended with extragranular portions of sodium bicarbonate, calcium carbonate, mannitol, crospovidone XL, hypromellose (or sodium alginate, or a mixture of hypromellose and sodium alginate, or a carbomer (CARBOPOL)), colloidal silicon dioxide, and magnesium stearate, and granulated by dry granulation process such as slugging followed by milling. The final granulate blend is then compressed into a tablet core using a suitable tablet press.

Example 3: Seal Coated Tablet Core

Levodopa/carbidopa tablet cores (e.g., tablet cores F, Q, R, and S) were seal coated with an aqueous dispersion of OPADRY®.

TABLE 4

Formulation of seal coated tablet cores:

| Ingredient | Seal Coated Tablet Core 1 (mg) | Seal Coated Tablet Core 2 (mg) | Seal Coated Tablet Core 3 (mg) | Seal Coated Tablet Core 4 (mg) |
|---|---|---|---|---|
| Levodopa/carbidopa tablet core (F) | 1000.0 | | | |
| Levodopa/carbidopa tablet core (Q) | | 950.0 | | |
| Levodopa/carbidopa tablet core (R) | | | 830.0 | |
| Levodopa/carbidopa tablet core (S) | | | | 950.0 |
| Aqueous dispersion OPADRY ® II (85F19250)-15% w/w | 30.0 | 30.0 | 25.0 | 30.0 |
| Total tablet weight | 1030.0 | 980.0 | 855.0 | 980.0 |

Manufacturing Procedure:
1. OPADRY® II was added to water in a stainless steel container and mixed to form a uniform dispersion.
2. Co-granulate tablet cores (Tablet cores F, Q, R, and S) were coated using a partially perforated pan coater with an inlet air temperature of 40° C.-60° C. at a product temperature of 35-45° C.
3. The coated tablets were dried in the coating pan after completion of coating.

Example 4A: Functional Coated Tablet (with Surfactant)

Tablet cores (seal coated and non-seal coated) were coated with a functional coat comprising EUDRAGIT® RL 30D and KOLLICOAT® SR 30D; or EUDRAGIT® RL 30D and EUDRAGIT® NE 30D. The coating suspension was prepared by mixing a dispersion of EUDRAGIT® RL 30D with a dispersion of KOLLICOAT® SR 30D; or mixing a dispersion of EUDRAGIT® RL 30D with a dispersion of EUDRAGIT® NE 30D. The following methodology ensured uniformity of the dispersion.

TABLE 5

Formulation of functional coated tablets (with surfactant)

| Ingredients (mg/tab) | A' | B' | C' | D' | E' (NE:RL, 50:50, 20% TEC) | F' (NE:RL, 30:70, 10% TEC) | G' (NE:RL, 30:70, 20% TEC) |
|---|---|---|---|---|---|---|---|
| Seal coated core 1 | 1030.0 | 1030.0 | 1030.0 | 1030.0 | — | — | — |
| Non-seal coated cores (A-P) | — | — | — | — | 1000.0 | 1000.0 | 1000.0 |
| EUDRAGIT® RL 30D | 74.7 | 74.7 | 80.0 | 70.0 | 43.01 | 57.5. | 55.3 |
| KOLLICOAT® SR 30D | 32.1 | — | — | 30.0 | — | — | — |
| EUDRAGIT® NE 30D | — | 32.1 | 20.0 | — | 43.01 | 24.6 | 23.7 |
| Polysorbate 80 | 0.6 | 0.6 | 0.6 | 0.6 | 1.08 | 1.4 | 1.3 |
| Povidone | 10.7 | 10.7 | 20.0 | 20.0 | — | — | — |
| Triethyl citrate | 21.4 | 21.4 | 20.0 | 20.0 | 4.30 | 4.1 | 7.9 |
| Talc | 10.7 | 10.7 | 10.0 | 10.0 | 8.60 | 12.4 | 11.8 |
| Total | 1180.0 | 1180.0 | 1180.0 | 1180.0 | 1100.0 | 1100.0 | 1100.0 |

Manufacturing Procedure:

1. In a suitable container that contains the required amount of purified water, a weighed quantity of polysorbate 80 was added. Mixing was continued for ~5 minutes to obtain a clear solution.
2. Povidone was added to the solution from step #1, and the resulting solution was stirred for at least 10 minutes.
3. EUDRAGIT® RL 30D dispersion was added to povidone-containing solution from step #2 to form a homogeneous dispersion. The dispersion was mixed for 5 minutes.
4. To the dispersion in step #3, KOLLICOAT® SR 30D or EUDRAGIT® NE 30D dispersion was added and the resulting dispersion was stirred for at least 5 minutes.
5. To the dispersion from step #4, triethyl citrate and talc were added, and the resulting dispersion was mixed for ~45 minutes to obtain a homogeneous dispersion.
6. The homogeneous dispersion from step #5 was sprayed onto the seal coated, or non-seal coated, tablet core.
7. The coated tablets from step #6 were dried in a coating pan.
8. The coated tablets were dried at 40° C. for ~2 hours to ensure the removal of residual water and cure the coating.

Example 4B: Functional Coated Tablet (without Surfactant)

Tablet cores (seal coated and non-seal coated) were coated with a functional coat comprising EUDRAGIT® RL 30D and KOLLICOAT® SR 30D; or EUDRAGIT® RL 30D and EUDRAGIT® NE 30D. The coating suspension was prepared by mixing a dispersion of EUDRAGIT® RL 30D with a dispersion of KOLLICOAT® SR 30D, or mixing a dispersion of EUDRAGIT® RL 30D with a dispersion of EUDRAGIT® NE 30D. The following methodology ensured uniformity of the dispersion.

TABLE 6

Formulation of functional coated tablets (without surfactants)

| Ingredients | H' (mg) | I' (mg) | J' (mg) | K' (mg) | L' (mg) | M' (mg) | N' (mg) | O' (mg) |
|---|---|---|---|---|---|---|---|---|
| Non-seal coated cores (A-P) | — | — | — | — | — | — | 1000.0 | 1000.0 |
| Seal coated core 1 | 1030.0 | 1030.0 | 1030.0 | 1030.0 | 1030.0 | 1030.0 | — | — |
| EUDRAGIT® RL 30D | 75.0 | 75.0 | 70.0 | 80.0 | 75.0 | 41.2 | 60.8 | 56.4 |
| KOLLICOAT® SR 30D | 32.2 | — | — | — | — | — | 18.2 | 16.9 |
| EUDRAGIT® NE 30D | — | 32.2 | 30.0 | 20.0 | 18.75 | 17.6 | — | — |
| Dilute hydrochloric acid/purified water | qs to pH 2.0 (removed during coating process) | | | | | | | |
| Povidone | 10.7 | 10.7 | 20.0 | 20.0 | 28.1 | 23.5 | — | — |
| Triethyl citrate | 21.4 | 21.4 | 20.0 | 20.0 | 18.75 | 11.8 | 7.9 | 14.7 |
| Talc | 10.7 | 10.7 | 10.0 | 10.0 | 9.4 | 5.9 | 13.1 | 12.0 |
| Total | 1180.0 | 1180.0 | 1180.0 | 1180.0 | 1180.0 | 1130.0 | 1100.0 | 1100.0 |

Manufacturing Procedure:

1. The required amount of purified water was weighed in a suitable container. The pH of the water was adjusted to about 2.0 by addition of dilute hydrochloric acid. The resultant solution was mixed for about 5 minutes.
2. Povidone was added to the solution from step #1, and the resulting solution was stirred for at least 10 minutes.
3. EUDRAGIT® RL 30D dispersion was added to povidone-containing purified water from step #2 to form a homogeneous dispersion at 15.34% solid content. The resulting dispersion was mixed for ~5 minutes.
4. To this dispersion, in step #3, KOLLICOAT® SR 30D or EUDRAGIT® NE 30D was added and the resulting dispersion was stirred for at least 5 minutes.

5. To the dispersion from step #4, triethyl citrate and talc were added, and the resulting dispersion was mixed for ~45 minutes to obtain a homogeneous dispersion. A uniform dispersion of 21% solid content was obtained.
6. The homogeneous dispersion from step #5 was sprayed onto the seal coated, or non-seal coated, tablet core.
7. The coated tablets from step #6 were dried in a coating pan.
8. The coated tablets were dried at 40° C. for ~2 hours to ensure the removal of residual water and cure the coating.

Example 5: Functional Coated Tablet (without Surfactant)

Seal coated tablet cores (Example 3) were coated with a functional coat comprising EUDRAGIT® RL 30D and EUDRAGIT® NE 30D. The coating suspension was prepared by mixing a dispersion of EUDRAGIT® RL 30D with a dispersion of KOLLICOAT® SR 30D, or mixing a dispersion of EUDRAGIT® RL 30D with a dispersion of EUDRAGIT® NE 30D. The following methodology ensured uniformity of the dispersion.

TABLE 7

Functional coated tablets

| Ingredients | Functional Coated Tablet 2 (mg) | Functional Coated Tablet 3 (mg) | Functional Coated Tablet 4 (mg) |
|---|---|---|---|
| Seal coated core (Cores 2, 3, and 4) | 980.0 | 855.0 | 980.0 |
| EUDRAGIT ® RL 30D | 103.8 | 89.95 | 79.58 |
| EUDRAGIT ® NE 30D | 11.60 | 10.05 | 8.890 |
| Triethyl citrate | 23.0 | 19.93 | 17.63 |
| Talc | 11.60 | 10.05 | 8.890 |
| Dilute hydrochloric acid, NF (HCl 10%)* | 12.20 | 10.57 | 9.350 |
| Purified water, USP | — | — | — |
| Total | 1130.0 | 985.0 | 1095.0 |

*Totals do not include stated amount of acid.

Manufacturing Procedure:
1. Required amount of purified water was weighed in a suitable container. The pH of the water was adjusted to about 2.0 by addition of dilute hydrochloric acid. The resultant solution was mixed for ~5 minutes.
2. EUDRAGIT® RL 30D dispersion was added to the solution from step #1 to form a homogeneous dispersion. The resulting dispersion was mixed for ~5 minutes.
3. To the dispersion in step #2, EUDRAGIT® NE 30D was added and the resulting dispersion was stirred for at least 5 minutes.
4. To the dispersion from step #3, triethyl citrate was added and mixed for at least 5 minutes followed by addition of talc and mixing for at least 60 minutes.
5. The homogeneous dispersion from step #4 was sprayed onto the seal coated, or non-seal coated, tablet core.
6. The coated tablets from step #5 were dried in a coating pan.

Example 6: Functional Coated Tablet

Seal coated tablet core Q was coated with a functional coat comprising EUDRAGIT® RL PO.

TABLE 8

Functional coated tablets

| Ingredients | Functional Coated Tablet 5 (mg) |
|---|---|
| Seal coated core (Q) | 980.0 |
| EUDRAGIT ® RL PO | 51.85 |
| Triethyl citrate | 7.78 |
| Talc | 10.37 |
| Acetone:water (95:5) | — |
| Total | 1050.0 |

Manufacturing Procedure:
1. EUDRAGIT® RL PO was added to acetone:water (95:5) mixture and mixed for at least 30 minutes.
2. To the solution from step #1, triethyl citrate was added and mixed for at least 30 minutes.
3. To the solution from step #2, talc was added and mixed for at least 30 minutes to obtain a homogeneous dispersion.
4. The homogeneous dispersion from step #3 was sprayed onto the seal coated tablet core.
5. The coated tablets from step #4 were dried in a coating pan.

Example 7: Immediate Release Layer/Overcoat

The functional coated tablets from Example 4B (e.g., K' and L') and Example 6 (Tablet 5) were further coated with an overcoat (6-I and 6-VI respectively). The overcoat can optionally comprise an IR portion of levodopa and carbidopa (6-II-6-V).

TABLE 9

Formulation of overcoated tablets

| Ingredients | 6-I | 6-II | 6-III | 6-IV | 6-V | 6-VI |
|---|---|---|---|---|---|---|
| | | | (mg) | | | |
| Functional Coated Tablet | 1180.0 | 1180.0 | 1180.0 | 1180.0 | 1180.0 | 1050.0 |
| Levodopa | — | 50.0 | 50.0 | 50.0 | 50.0 | — |
| Carbidopa | — | 12.5 | 12.5 | 12.5 | 12.5 | — |
| Alpha-tocopherol | — | — | 5.0 | — | — | — |
| Tartaric acid | — | — | — | 5.0 | — | — |
| 0.1N Hydrochloric acid | — | — | — | — | 5.0 | — |
| Hypromellose | — | 5.0 | 5.0 | 5.0 | 5.0 | — |
| Ethyl alcohol | — | — | 100.0* | — | — | — |

TABLE 9-continued

Formulation of overcoated tablets

| Ingredients | 6-I | 6-II | 6-III | 6-IV | 6-V | 6-VI |
|---|---|---|---|---|---|---|
| | (mg) | | | | | |
| Purified Water* | — | 270.0* | 170.0* | 270.0* | 270.0* | — |
| OPADRY ® II Complete Coating System | 20.0 | 20.0 | 20.0 | 20.0 | 20.0 | 25.0 |
| Purified water | 80.0* | 80.0* | 80.0* | 80.0* | 80.0* | 80.0 |
| Total weight | 1200.0 | 1267.5 | 1272.5 | 1272.5 | 1272.5 | 1075.0 |

*Removed during processing.

Manufacturing Process (6-I & 6 VI):
1. Weighed quantity of OPADRY® II was added into the required amount of purified water. The suspension was mixed until a uniform dispersion was formed.
2. The functional coated tablets (i.e., tablets K' and L', and Tablet 5) were further coated with the above dispersion in a perforated coating pan with inlet air temperature at 40°-45° C.
3. The tablets were dried in a pan to a moisture content below 1.5%, as measured by loss on drying at 105° C.

Manufacturing Process (6-II):
1. Weighed amount of hypromellose was dispersed in purified water and stirred until a clear solution as obtained.
2. Levodopa and carbidopa were dispersed in the solution from step #1.
3. The drug-containing suspension was coated onto the functionally coated tablets from Example 4B.
4. The drug coated tablets from step #3 were dried in the film coater at 40-45° C. for ~30 min before proceeding to apply the overcoat using the same procedure as described in 6-I (above).

Manufacturing Process (6-III):
1. Weighed amount of hypromellose was dispersed in purified water and stirred until a clear solution was obtained.
2. Weighed amount of alpha-tocopherol was dissolved in the required quantity of ethyl alcohol. The solution of alpha-tocopherol was added to the solution of hypromellose from step #1.
3. Levodopa and carbidopa were dispersed in the solution from step #2.
4. The drug-containing suspension was coated onto the functionally coated tablets from Example 4B.
5. The drug coated tablets from step #4 were dried in the film coater at 40-45° C. for ~30 min before proceeding to apply the overcoat using the same procedure as described in 6-I.

Manufacturing Process (6-IV and 6-V):
1. Weighed amount of tartaric acid or 0.1N hydrochloric acid was added to the purified water.
2. Weighed quantity of hypromellose was dissolved in the acidified water solution from Step #1.
3. Levodopa and carbidopa were dispersed in the solution from step #2.
4. The drug-containing suspension was coated onto the functionally coated tablets from Example 3B.
5. The drug coated tablets were dried in the film coater at 40-45° C. for ~30 min before proceeding to apply the overcoat using the same procedure as described in 6-I.

Example 8: Overcoat

The functional coated tablets from Example 5 (Tablets 2 and 4) were further coated with an overcoat.

TABLE 10

Formulation of overcoated tablets

| Ingredients | Tablet 2 with Overcoat (mg) | Tablet 4 with Overcoat (mg) |
|---|---|---|
| Functional Coated Tablet | 1130.0 | 1095.0 |
| OPADRY ® II, Pink | 25.00 | 25.00 |
| Total | 1155.0 | 1120.0 |

Manufacturing Process:
1. Weighed quantity of Opadry II was added into the required amount of purified water. The suspension was mixed until a uniform dispersion was formed.
2. The tablets coated with functional coat (Tablets 2 and 4) were further coated with the above dispersion in a perforated coating pan with inlet air temperature at 40°-60° C. at an exhaust air temperature of 35° C.-45° C.

Example 9: Immediate Release (IR) Layer

The functional coated tablets from Example 5 (Tablet 3) were further coated with a seal coat and an immediate release layer comprising an IR portion of levodopa and carbidopa.

TABLE 11

Formulation of tablet with seal coat

| Ingredients | Tablet 3 with Functional Coat and Seal Coat (mg) |
|---|---|
| Functional Coated Tablet 3 | 985.0 |
| OPADRY II Clear | 30.0 |
| Purified water, USP | — |
| Total | 1015.0 |

TABLE 12

Formulation of tablet with immediate release (IR) layer

| Ingredients | Tablet 3 with IR Layer (mg) |
|---|---|
| Functional Coated tablets further coated with Seal Coat (Tablet 3-Table 11) | 1015.0 |

TABLE 12-continued

Formulation of tablet with immediate release (IR) layer

| Ingredients | Tablet 3 with IR Layer (mg) |
| --- | --- |
| Carbidopa, USP | 6.75 |
| Levodopa, USP | 25.00 |
| Hydroxypropyl cellulose | 5.80 |
| dl-α-tocopherol | 0.20 |
| Succinic acid, NF (Crystal) | 1.250 |
| Ethanol (200 proof, absolute) | — |
| Total | 1054.0 |

TABLE 13

Formulation of tablet with seal coat over IR layer

| Ingredients | Tablet 3 with Seal Coat over the IR layer (mg) |
| --- | --- |
| Tablet with IR layer (Tablet 3-Table 12) | 1054 |
| OPADRY II Clear | 16.00 |
| Purified water, USP | — |
| Total | 1070.0 |

TABLE 14

Formulation of tablet with overcoat over IR Layer/seal coat

| Ingredients | Tablet 3 with IR layer, Seal Coat, and Overcoat (mg) |
| --- | --- |
| Tablet with seal coat over IR layer (Tablet 3-Table 13) | 1070.0 |
| OPADRY II, Pink | 25.00 |
| Purified water, USP | — |
| Total | 1095.0 |

1. Functional coated tablet 3 was coated with a seal coat as described in Example 3 to obtain a seal coat over functional coated tablet 3.
2. Weighed amount of succinic acid was dispersed in ethanol and stirred until a clear solution was obtained.
3. Hydroxypropyl methylcellulose was slowly added to the solution from step #2 and mixed until a clear solution was obtained.
4. A weighed amount of dl-α-tocopherol was added to the solution from step #3 and mixed until a clear solution was obtained.
5. Levodopa and carbidopa were dispersed into the solution from step #4 and the resulting dispersion was mixed.
6. The dispersion from step #5 was screened through #45 mesh to obtain a uniform drug coating suspension.
7. The drug coating suspension from step #6 was coated onto the seal coat over the functional coated tablets from step #1.
8. The coated tablets from step #7 were dried in a coating pan before proceeding to apply a seal coat and an overcoat above the IR coat using the same procedure as described above in Examples 3 and 7 respectively.

Example 10: Measurement of Gravimetric Swelling

Coated tablet, e.g., Tablets 2 and 4 (Example 8), Tablet 3 (Example 9), was placed in 200 mL of 0.01 N hydrochloric acid in a rotating bottle apparatus at 15 rpm, and at a temperature of 37° C.

Weight of the tablet from step #1 was measured at specified time intervals, i.e., 0, 2, 4, 6, 8, 10, 12, 14, and 16 hours, and the percent gravimetric gain was calculated using the following equation:

$$\text{Gravimetric Gain (\%)} = \frac{W_s - W_d}{W_d} \times 100$$

wherein $W_s$ is the weight of swollen tablet (at specific time point), $W_d$ is weight of dry tablet (initial).

FIG. 9 demonstrates tablet weight gain of Tablets 2, 3, and 4 over a 14-hour period.

Example 11: Measurement of Volumetric Swelling

The tablet volume was determined to calculate the volumetric expansion. To calculate the volume, swollen tablet was placed in a graduated measuring cylinder filled with a fixed volume of 0.01 N HCl and the rise in HCl level was noted over a 14 hour-period. The percent volumetric expansion was calculated using the following equation:

$$\text{Volumetric Gain (\%)} = \frac{V_s - V_d}{V_d} \times 100$$

$V_s$ is the volume of swollen tablet (at specific time point), and $V_d$ is the volume of dry tablet (initial).

FIG. 10 demonstrates tablet volume gain of Tablets 2 and 4 (Example 8), and Tablet 3 (Example 9) over a 14-hour period. FIG. 10 shows that the tablets exhibit a volume gain of more than 300% in less than 1 hour.

With reference to FIG. 19 for the purpose of illustration and not limitation, there is provided a volumetric swelling profile demonstrating a tablet volume gain for Levodopa/Carbidopa Tablet 6-VI (Example 7) over about an 1100-minute (18-hour) period. FIG. 19 shows tablet volume gain of 425% in about 60 minutes.

Example 12: Measurement of Floating Lag Time

The time required for the tablet to float in gastric medium is an important measure of the gastric retention, as a rapid progression to floating reduces the chance of accidental emptying escape of the dosage form from the stomach. The floating time was measured in the same experiment as illustrated above with volumetric and gravimetric swelling.

FIG. 4 shows the floating lag time for Tablets 2 and 4 (Example 8), and Tablet 3 (Example 9) in 0.01N HCl and pH 4.5 acetate buffer, measured in a rotating bottle apparatus method. The tablets show a floating lag time of about 12 minutes or less.

Floating lag time of Levodopa/Carbidopa Tablet 6-VI, measured using biodisk reciprocating cylinder apparatus, at 15 rpm, 25 dpm, in 250 ml of pH 4.5 acetate buffer is about 6 minutes.

Example 13: Measurement of Dissolution Profile

Dissolution of drug from the dosage form is an important measure to achieve controlled and sustained delivery of the drug. The dissolution studies were performed using different conditions to assess the effect of different physiological and hydrodynamic conditions with regards to pH, buffer species, and shear forces. The United States Pharmacopeia (USP) has established standardized dissolution apparatus to measure the in vitro performance of a drug product for development and quality control purposes. These standard procedures use in vitro solubility as a surrogate for in vivo absorption. Because of the floating nature of the tablet, USP apparatus I, which uses a basket as sample holder, was used to evaluate the release of drug from these tablets as a function of time. In addition, to simulate the effect of different shear conditions under fasting and fed states, dissolution studies were also performed in a rotating bottle apparatus, and biodisk reciprocating cylinder method at different speeds. Different dissolution methods used for this purpose are described below:

USP Apparatus I (Basket Method): A Distek Automatic Dissolution Apparatus equipped with online UV measurement was used. The dissolution test was performed in 900 mL of 0.1N hydrochloric acid with pH 1.5 to simulate the fasted conditions at 37° C., and pH 4.5 acetate buffer to simulate fed conditions. A rotation speed of 100 rpm was used. In the case of a combination product such as carbidopa/levodopa, the drug release was measured using High Performance Liquid Chromatography (HPLC). Drug sample (5 ml) was withdrawn at specified time intervals of 2, 4, 6, 8, 10, 12, 14, 16, 20, and 24 hrs, and the drug content was measured by HPLC. For singular (non-combination) drug products, the tablet is placed in the rotating basket and release of the drug is measured using online UV spectroscopy. FIGS. 15 and 16 show custom basket dissolution profiles of carbidopa and levodopa respectively from Tablet 6-VI in 900 ml of pH 4.5 acetate buffer. The figures demonstrate at least about 10% dissolution of levodopa and carbidopa in a dissolution medium simulating a fed state of an individual, in less than about 120 minutes.

FIG. 20 shows a custom basket dissolution profile of pyridostigmine bromide from Pyridostigmine Tablets 1, 2, and 3 in 900 ml of pH 4.5 acetate buffer. The figure demonstrates at least about 20% dissolution of pyridostigmine bromide in about 2 hours.

Rotating Bottle Method: A rotating bottle method was used to simulate high shear conditions in stomach. The tablet (core F, seal coat, functional coat K, overcoat 6-I) was placed in 200 ml of dissolution medium in a glass bottle containing 10 g of glass beads (3 mm). The bottle was secured in the rotating arm of an apparatus placed inside a constant temperature water bath maintained at 37° C. The bottle was rotated at speeds of 15 rpm or 30 rpm to simulate the effect of different shear conditions in the stomach in fed state. Drug sample (5-10 ml) was withdrawn at specified time intervals of 2, 4, 6, 8, 14, and 16 hrs, and the drug content released was measured using HPLC. Dissolution tests were performed in 0.1N hydrochloric acid, and in pH 4.5 acetate buffer.

Figure 5:
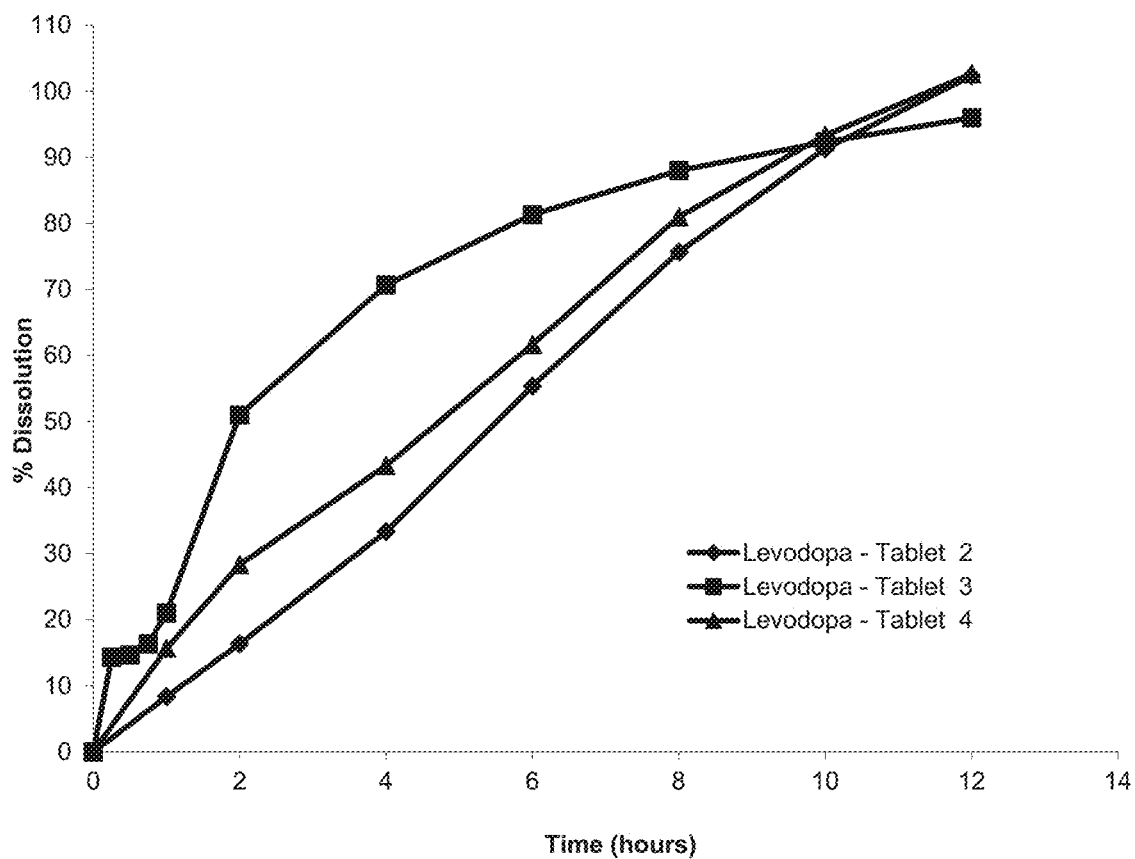
FIG. 5 shows rotating bottle dissolution profiles of Levodopa Tablets 2, 3, and 4, at 15 rpm, in 200 ml 0.01N HCl.
Figure 6:
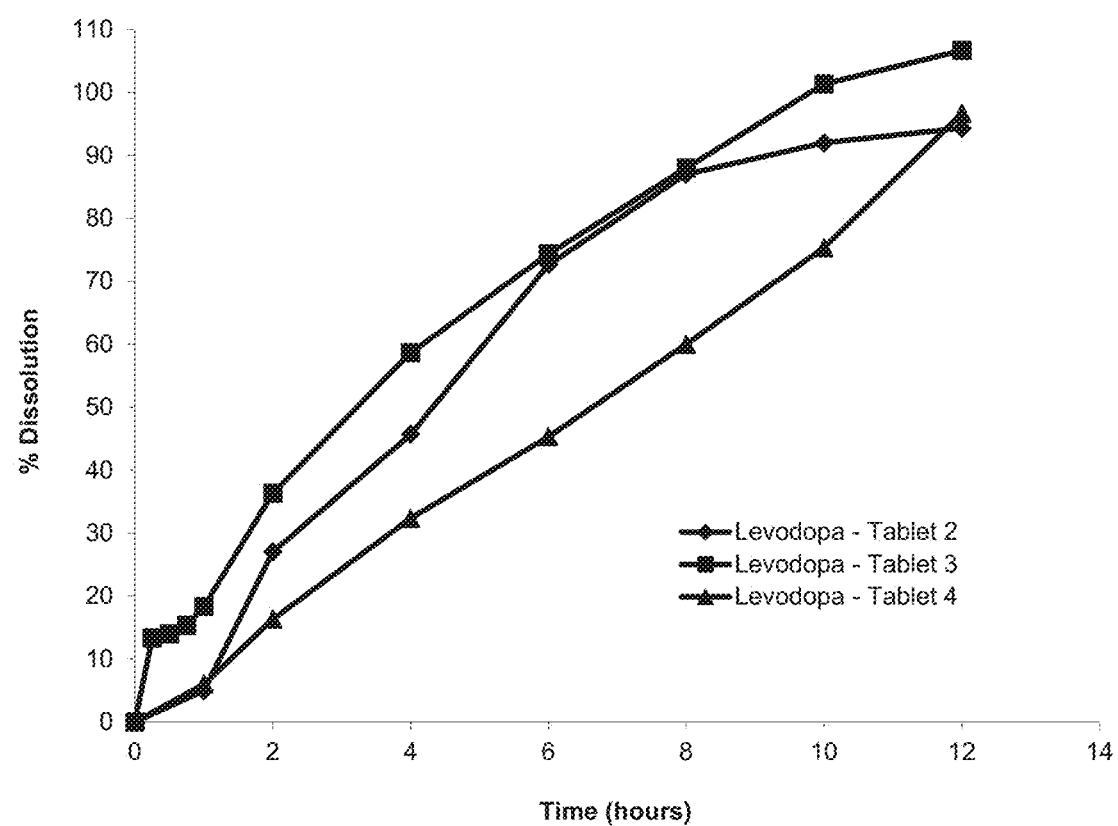
FIG. 6 shows rotating bottle dissolution profiles of Levodopa Tablets 2, 3, and 4, at 15 rpm, in 200 ml pH 4.5 acetate buffer.

FIGS. 5 and 6 show rotating bottle dissolution profiles of levodopa from Tablets 2 and 4 (Example 8) and Tablet 3 (Example 9) in 200 ml 0.01 N HCl and in pH 4.5 acetate buffer, respectively. Similarly, FIGS. 11 and 12 show rotating bottle dissolution profiles of carbidopa and levodopa respectively from Tablet 6-VI in 200 mls, pH 4.5 acetate buffer. Drug sample was withdrawn at specified time intervals of 2, 4, 6, 8, 10, 12, and 14 hrs, and the drug content released was measured using HPLC.

FIG. 7 shows a cyclic dissolution profiles of levodopa, simulating gastric conditions during a 12-hour period, e.g., fasted state, fed state, followed by fasted state, conducted for Tablets 2, 3, and 4. FIG. 7 shows the dissolution profile of Tablets 2 and 4 (Example 8), and Tablet 3 (Example 9) in 0.01 N HCl for 4 hours, followed by dissolution in pH 4.5 acetate buffer for 4 hours, and final dissolution in 0.01 N HCl for 4 hours.

FIG. 8 shows cyclic dissolution profile of levodopa, simulating gastric conditions during a 12-hour period, e.g., fed state, fasted state, followed by fed state, conducted for Tablets 2, 3, and 4. FIG. 8 shows the dissolution profile of Tablets 2 and 4 (Example 8), and Tablet 3 (Example 9) in pH 4.5 acetate buffer for 4 hours, followed by dissolution in 0.01 N HCl for 4 hours, and final dissolution in pH 4.5 acetate buffer for 4 hours.

FIGS. 5-8 demonstrate about 15% dissolution of levodopa, in a dissolution medium simulating a fed or fasted state of an individual, in less than about 2 hours. FIG. 11 demonstrates about 8% dissolution of carbidopa, in a dissolution medium simulating a fed or fasted state of an individual, in about 1 hour. FIG. 12 demonstrates about 8% dissolution of levodopa, in a dissolution medium simulating a fed or fasted state of an individual, in about 1 hour.

USP Apparatus III-Biodisk Reciprocating Cylinder Method: A reciprocating cylinder method, associating the hydrodynamics of rotating bottle method with the facility for exposing the dosage form to different dissolution media and agitation speeds, was used to simulate high shear conditions in stomach. The dosage unit was inserted into an internal cylinder, consisting of a glass tube closed at both ends with plastic caps containing a screen. The internal cylinder was connected to metallic rod that undertook immersion and emersion movements (reciprocating action) within the dissolution vessel/external cylinder. In some embodiments, an anti-evaporation system is deployed over the vessels in order to avoid alteration in the volume of the dissolution medium during the assay. FIGS. 13 and 14 show dissolution profiles of carbidopa and levodopa respectively from Tablet 6-VI (Example 7) in pH 4.5 acetate buffer. Drug samples were withdrawn at specified time intervals of 2, 4, 6, 8, and 14 hours and drug concentration was measured using HPLC. FIGS. 13 and 14 demonstrate at least about 10% dissolution of carbidopa and levodopa in a dissolution medium simulating a fed state of an individual, in less than about 2 hours.

FIGS. 17 and 18 show cyclic dissolution profiles simulating gastric conditions during a 12-hour period, e.g., fed state, fasted state, followed by fed state, for Tablet 6-VI (Example 7). The figures provide cyclic dissolution profiles in pH 4.5 acetate buffer, followed by dissolution in 0.01 N HCl, and final dissolution in pH 4.5 acetate buffer, of carbidopa and levodopa, respectively, from Tablet 6-VI (Example 7).

Example 14: Pyridostigmine Tablet Core

Tablet cores were prepared for use in 180 mg pyridostigmine dosage forms.

TABLE 15

Formulation of pyridostigmine tablet core

| Ingredients | Tablet Core 1 (mg) | Tablet Core 2 (mg) | Tablet Core 3 (mg) |
| --- | --- | --- | --- |
| Pyridostigmine | 180.0 | 180.0 | 180.0 |
| Succinic acid | 50.0 | 50.0 | 50.0 |
| Sodium bicarbonate | 50.00 | 50.0 | 50.0 |
| Calcium carbonate | 125.0 | 125.0 | 125.0 |

TABLE 15-continued

Formulation of pyridostigmine tablet core

| Ingredients | Tablet Core 1 (mg) | Tablet Core 2 (mg) | Tablet Core 3 (mg) |
|---|---|---|---|
| Crospovidone | 100.0 | 100.0 | 100.0 |
| Parteck 200 | 233.0 | 233.0 | 233.0 |
| Benecel, K4M-DC | 200.0 | 300.0 | 200.0 |
| Benecel, K200M | NA | NA | 25.0 |
| Cab-O-Sil | 4.00 | 4.00 | 4.00 |
| Magnesium stearate | 8.00 | 8.00 | 8.00 |
| Total weight | 950.0 | 1050.0 | 975.0 |

Manufacturing Procedure:

1. Pyridostigmine, succinic acid, sodium bicarbonate, calcium carbonate, crospovidone, Parteck 200, Benecel K4M-Dca, Benecel K200M, and Cab-O-Sil, as per Tablet Cores 1-5, were sieved through filter #20 and mixed to obtain a uniform blend.
2. Magnesium stearate was sieved through sieve #30 and mixed with the uniform blend from step #1.
3. The resulting blend from step #2 was compressed to obtain pyridostigmine tablet core.

Example 15: Seal Coated Pyridostigmine Tablet Core

Pyridostigmine tablet cores from Example 14 were seal coated with a dispersion of hydroxypropyl cellulose, triethyl citrate, and talc.

TABLE 16

Formulation of seal coated tablet cores:

| Ingredient | Tablet Core 1 (mg) | Tablet Core 2 (mg) | Tablet Core 3 (mg) |
|---|---|---|---|
| Pyridostigmine tablet core | 950.0 | 1050.0 | 975.0 |
| Hydroxypropyl cellulose | 33.33 | 33.33 | 33.33 |
| Talc | 3.33 | 3.33 | 3.33 |
| Triethyl citrate | 3.33 | 3.33 | 3.33 |
| Acetone & water (95:5) | — | — | — |
| Total tablet weight | 989.99 | 1089.99 | 1014.99 |

Manufacturing Procedure:

1. Hydroxypropyl cellulose, triethyl citrate, and talc were added to a mixture of acetone and water (95:5 v/v ratio) in a stainless steel container and mixed to form a uniform dispersion.
2. Tablet cores from Example 14 were seal coated using a partially perforated pan coater with an inlet air temperature of 40° C.-60° C. at a product temperature of 35-45° C.
3. The coated tablet cores were dried in the coating pan.

Example 16: Functional Coated Pyridostigmine Tablet Core with an Overcoat

Seal coated tablet cores were coated with a functional coat comprising EUDRAGIT® RL PO and an overcoat.

TABLE 17

Formulation of Functional Coated Tablet Cores with 200 mg Coating Weight Gain:

| Ingredient | Tablet 1 (mg) | Tablet 2 (mg) | Tablet 3 (mg) |
|---|---|---|---|
| Seal coated pyridostigmine tablet core | 989.99 | 1089.99 | 1014.99 |
| EUDRAGIT$^R$ RL PO | 148.15 | 148.15 | 148.15 |
| Triethyl citrate | 22.22 | 22.22 | 22.22 |
| Talc | 29.63 | 29.63 | 29.63 |
| Acetone:Water (95:5) | — | — | — |
| Purified water qs | — | — | — |
| Overcoat | | | |
| Opadry white | 15.00 | 15.00 | 15.00 |
| Total tablet weight | 1205.0 | 1305 | 1230.00 |

Manufacturing Procedure:

1. EUDRAGIT® RL PO was added to acetone and water mixture (95:5) and mixed to obtain a clear solution.
2. To the solution from step #1, triethyl citrate was added and mixed for at least 5 minutes.
3. To the solution from step #2, talc was added and mixed for at least 60 minutes to obtain a homogeneous dispersion.
4. The homogeneous dispersion from step #3 was sprayed onto the seal coated tablet cores.
5. The coated tablets from step #4 were dried in a coating pan.
6. An orifice was laser drilled in the coated tablets from step #5 such that the orifice passed through various coating layers and tablet core.
7. Weighed quantity of Opadry II was added into the required amount of purified water. The suspension was mixed until a uniform dispersion was formed.
8. The functional coated tablets from step #6 were further coated with the dispersion from step #7 in a perforated coating pan with inlet air temperature at 40°-45° C.
9. The coated tablets from step #8 were dried in a pan to a moisture content below 1.5%, as measured by loss on drying at 105° C.

Example 17: Metaxalone Tablet Core

Tablet cores are prepared for use in 200 mg and 400 mg metaxalone dosage forms.

TABLE 18

Formulation of metaxalone tablet core

| Ingredients | Tablet Core 1 (mg) | Tablet Core 2 (mg) |
|---|---|---|
| Intragranular | | |
| Metaxalone | 200.0 | 400.0 |
| Mannitol | 120.0 | 120.0 |
| Hydroxypropyl cellulose | 8.00 | 8.00 |
| dl-α-tocopherol | 0.500 | 0.500 |
| Succinic acid | 50.00 | 50.00 |
| Ethyl alcohol 200 proof, absolute | — | — |
| Extragranular | | |
| Sodium bicarbonate | 50.00 | 50.00 |
| Calcium carbonate | 125.0 | 125.0 |
| Crospovidone, NF (Polyplasdone XL) | 100.0 | 100.0 |
| Mannitol | 134.5 | 134.5 |
| Hypromellose | 50.00 | 50.00 |

TABLE 18-continued

Formulation of metaxalone tablet core

| Ingredients | Tablet Core 1 (mg) | Tablet Core 2 (mg) |
|---|---|---|
| Magnesium stearate | 8.00 | 8.00 |
| Colloidal silicon dioxide (CABOSIL) | 4.00 | 4.00 |
| Total | 850.0 | 1050.0 |

Manufacturing Procedure:

1. Preparing metaxalone granules: Metaxalone granules are made by high shear wet granulation process. Metaxalone, mannitol, hydroxypropyl cellulose, and succinic acid are placed in a high shear granulator and mixed into a uniform powder blend. The powder blend is wet granulated using ethanol and vitamin-E mixture as granulation fluid. The resulting wet granules are dried in a fluid bed dryer and milled using an impact mill to prepare uniform sized metaxalone granules.
2. Mixing with extragranular excipients: The metaxalone granules from Step #1 are blended with sodium bicarbonate, calcium carbonate, crospovidone XL, mannitol, hypromellose (or sodium alginate, or a mixture of hypromellose and sodium alginate, or a carbomer (CARBOPOL)), colloidal silicon dioxide, and magnesium stearate. The final blend is compressed into a tablet core using a suitable tablet press.

In an alternative process, the metaxalone granules obtained from Step #1 can be blended with extragranular portions of sodium bicarbonate, calcium carbonate, mannitol, crospovidone XL, hypromellose (or sodium alginate, or a mixture of hypromellose and sodium alginate, or a carbomer (CARBOPOL)), colloidal silicon dioxide and magnesium stearate, and granulated by dry granulation process such as slugging followed by milling. The final granulate blend is then compressed into a tablet core using a suitable tablet press.

Example 18: Seal Coated Tablet Core

Metaxalone tablet cores from Example 17 are seal coated with an aqueous dispersion of Opadry®.

TABLE 19

Formulation of seal coated tablet cores:

| Ingredients | Seal Coated Tablet Core 1 (mg) | Seal Coated Tablet Core 2 (mg) |
|---|---|---|
| Carvedilol tablet core 1 | 850 | |
| Carvedilol tablet core 2 | | 1050.0 |
| Aqueous dispersion Opadry II (85F19250)-15% w/w | 30.0 | 30.0 |
| Total tablet weight | 880.0 | 1080.0 |

Manufacturing Procedure:

1. Opadry II is added to water in a stainless steel container and mixed to form a uniform dispersion.
2. Metaxalone tablet cores (Tablet cores 1, 2) are coated using a partially perforated pan coater with an inlet air temperature of 40° C.-60° C. at a product temperature of 35-45° C. The coated tablets are dried in the coating pan after completion of coating.

Example 19

Seal coated tablet cores are coated with a functional coat comprising EUDRAGIT® RL PO.

TABLE 20

Functional coated tablets

| Ingredients | Functional Coated Tablet 1 (mg) | Functional Coated Tablet 2 (mg) |
|---|---|---|
| Seal coated core (1) | 880.0 | — |
| Seal coated core (2) | — | 1080 |
| EUDRAGIT ® RL PO | 51.85 | 51.85 |
| Triethyl citrate | 7.78 | 7.78 |
| Talc | 10.37 | 10.37 |
| Acetone:water (95:5) | — | — |
| Total | 950.0 | 1150.0 |

Manufacturing Procedure:

1. EUDRAGIT® RL PO is added to acetone:water (95:5) mixture and mixed for at least 30 minutes.
2. To the solution from step #1, triethyl citrate is added and mixed for at least 30 minutes.
3. To the solution from step #2, talc is added and mixed for at least 30 minutes to obtain a homogeneous dispersion.
4. The homogeneous dispersion from step #3 is sprayed onto the seal coated tablet core.
5. The coated tablets from step #4 are dried in a coating pan.

Example 20: Overcoat

The functional coated tablets are further coated with an overcoat

TABLE 21

Formulation of overcoated tablets

| Ingredients | Overcoated Tablet 1 (mg) | Overcoated Tablet 2 (mg) |
|---|---|---|
| Functional Coated Tablet | 950.0 | 1150.0 |
| Opadry II Complete Coating System | 20.0 | 20.0 |
| Purified water | 80.0* | 80.0* |
| Total weight | 970.0 | 1170.0 |

*Removed during processing.

Manufacturing Process (5 & 6):

1. Weighed quantity of Opadry II is added into the required amount of purified water. The suspension is mixed until a uniform dispersion is formed.
2. The functional coated tablets are further coated with the above dispersion in a perforated coating pan with inlet air temperature at 40°-45° C.
3. The tablets are dried in a pan to a moisture content below 1.5%, as measured by loss on drying at 105° C.

Example 21: Carvedilol Tablet Core

Tablet cores are prepared for use in 40 mg and 80 mg carvedilol dosage forms.

TABLE 22

Formulation of carvedilol tablet core

| Ingredients | Tablet Core 1 (mg) | Tablet Core 2 (mg) |
|---|---|---|
| Intragranular | | |
| Carvedilol | 40.0 | 80.0 |
| Mannitol | 130.0 | 140.0 |
| Hydroxypropyl cellulose | 8.00 | 8.00 |
| dl-α-tocopherol | 0.500 | 0.500 |
| Succinic acid | 50.00 | 50.00 |
| Ethyl alcohol 200 proof, absolute | — | — |
| Extragranular | | |
| Sodium bicarbonate | 50.00 | 50.00 |
| Calcium carbonate | 125.0 | 125.0 |
| Crospovidone, NF (Polyplasdone XL) | 100.0 | 100.0 |
| Mannitol | 134.5 | 134.5 |
| Hypromellose | 50.00 | 50.00 |
| Magnesium stearate | 8.00 | 8.00 |
| Colloidal silicon dioxide (CABOSIL) | 4.00 | 4.00 |
| Total | 700.0 | 750.0 |

Manufacturing Procedure:
1. Preparing carvedilol granules: Carvedilol granules are made by high shear wet granulation process. Carvedilol, mannitol, hydroxypropyl cellulose, and succinic acid are placed in a high shear granulator and mixed into a uniform powder blend. The powder blend is wet granulated using ethanol and vitamin-E mixture as granulation fluid. The resulting wet granules are dried in a fluid bed dryer and milled using an impact mill to prepare uniform sized carvedilol granules.
2. Mixing with extragranular excipients: The carvedilol granules from Step #1 are blended with sodium bicarbonate, calcium carbonate, crospovidone XL, mannitol, hypromellose (or sodium alginate, or a mixture of hypromellose and sodium alginate, or a carbomer (CARBOPOL)), colloidal silicon dioxide, and magnesium stearate. The final blend is compressed into a tablet core using a suitable tablet press.

In an alternative process, the carvedilol granulesles obtained from Step #1 can be blended with extragranular portions of sodium bicarbonate, calcium carbonate, mannitol, crospovidone XL, hypromellose (or sodium alginate, or a mixture of hypromellose and sodium alginate, or a carbomer (CARBOPOL)), colloidal silicon dioxide and magnesium stearate, and granulated by dry granulation process such as slugging followed by milling. The final granulate blend is then compressed into a tablet core using a suitable tablet press.

Example 22: Seal Coated Tablet Core

Carvedilol tablet cores from Example 21 are seal coated with an aqueous dispersion of Opadry®.

TABLE 23

Formulation of seal coated tablet cores:

| Ingredients | Seal Coated Tablet Core 1 (mg) | Seal Coated Tablet Core 2 (mg) |
|---|---|---|
| Carvedilol tablet core 1 | 700 | |
| Carvedilol tablet core 2 | | 750.0 |
| Aqueous dispersion Opadry II (85F19250)-15% w/w | 30.0 | 30.0 |
| Total tablet weight | 730.0 | 780.0 |

Manufacturing Procedure:
1. Opadry II is added to water in a stainless steel container and mixed to form a uniform dispersion.
2. Carvedilol tablet cores (Tablet cores 1, 2) are coated using a partially perforated pan coater with an inlet air temperature of 40° C.-60° C. at a product temperature of 35-45° C.
3. The coated tablets are dried in the coating pan after completion of coating.

Example 23

Seal coated tablet cores are coated with a functional coat comprising EUDRAGIT® RL PO.

TABLE 24

Functional coated tablets

| Ingredients | Functional Coated Tablet 1 (mg) | Functional Coated Tablet 2 (mg) |
|---|---|---|
| Seal coated core (1) | 880.0 | — |
| Seal coated core (2) | — | 1080 |
| EUDRAGIT ® RL PO | 51.85 | 51.85 |
| Triethyl citrate | 7.78 | 7.78 |
| Talc | 10.37 | 10.37 |
| Acetone:water (95:5) | — | — |
| Total | 950.0 | 1150.0 |

Manufacturing Procedure:
1. EUDRAGIT® RL PO is added to acetone:water (95:5) mixture and mixed for at least 30 minutes.
2. To the solution from step #1, triethyl citrate is added and mixed for at least 30 minutes.
3. To the solution from step #2, talc is added and mixed for at least 30 minutes to obtain a homogeneous dispersion.
4. The homogeneous dispersion from step #3 is sprayed onto the seal coated tablet core.
5. The coated tablets from step #4 are dried in a coating pan.

Example 24: Overcoat

The functional coated tablets were further coated with an overcoat.

TABLE 25

Formulation of overcoated tablets

| Ingredients | Overcoated Tablet 1 (mg) | Overcoated Tablet 2 (mg) |
|---|---|---|
| Functional Coated Tablet | 800.0 | 850.0 |
| Opadry II Complete Coating System (85F140066) | 20.0 | 20.0 |
| Purified water | 80.0* | 80.0* |
| Total weight | 820.0 | 870.0 |

*Removed during processing.

Manufacturing Process:
1. Weighed quantity of Opadry II is added into the required amount of purified water. The suspension is mixed until a uniform dispersion is formed.
2. The functional coated tablets are further coated with the above dispersion in a perforated coating pan with inlet air temperature at 40°-45° C.

3. The tablets are dried in a pan to a moisture content below 1.5%, as measured by loss on drying at 105° C.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

Patents, patent applications, publications, product descriptions, and protocols are cited throughout this application, the disclosures of which are incorporated herein by reference in their entireties for all purposes.

The invention claimed is:

1. A gastroretentive tablet dosage form comprising:
   a) a tablet core comprising pyridostigmine bromide, a swellable water-soluble hydrophilic polymer, and a gas-generating agent, and
   b) a coating of water-insoluble permeable elastic membrane comprising an orifice,
   wherein the coating surrounds the tablet core, and
   wherein the water-insoluble permeable elastic membrane comprises a plasticizer, and a copolymer of ethyl acrylate, methyl methacrylate, and trimethylammonioethyl methacrylate chloride.

2. The dosage form of claim 1, wherein the plasticizer is selected from the group consisting of triethyl citrate, triacetin, polyethylene glycol, propylene glycol, and mixtures thereof.

3. The dosage form of claim 1, wherein the plasticizer is present in an amount of from about 5% wt/wt to about 20% wt/wt, based on a total weight of the copolymer and the plasticizer.

4. The dosage form of claim 1, wherein the gas generating agent is present in an amount of from about 10% wt/wt to about 25% wt/wt, based on a total weight of the tablet core.

5. The dosage form of claim 1, wherein the tablet core further comprises an acid selected from the group consisting of, succinic acid, citric acid, acetic acid, malic acid, fumaric acid, stearic acid, tartaric acid, boric acid, benzoic acid, and mixtures thereof.

6. The dosage form of claim 1, wherein the dosage form exhibits at least about 20% dissolution of pyridostigmine bromide in 900 ml of 50 mM pH 4.5 acetate buffer, measured using USP Apparatus I (custom basket) at 100 rpm.

7. The dosage form of claim 1, wherein the dosage form provides extended release of pyridostigmine bromide for at least about 12 hours in 900 ml of 50 mM pH 4.5 acetate buffer, measured using USP Apparatus I (custom basket) at 100 rpm.

8. The dosage form of claim 1, wherein the tablet core further comprises a superdisintegrant selected from the group consisting of crospovidone; croscarmellose sodium; sodium starch glycolate; low substituted hydroxypropyl cellulose; microcrystalline cellulose; alginic acid; a mixture of mannitol, crospovidone, and polyvinyl acetate; a mixture of mannitol, starch, croscarmellose sodium, silica, and colloidal silica; and mixtures thereof.

9. The dosage form of claim 1, wherein the swellable water-soluble hydrophilic polymer in the tablet core is selected from the group consisting of hypromellose, hydroxyethyl cellulose, hydroxypropyl cellulose, carboxymethyl cellulose, microcrystalline cellulose, a polyethylene oxide polymer, and sodium alginate.

10. The dosage form of claim 1, wherein the gas-generating agent is selected from the group consisting of sodium bicarbonate, sodium carbonate, calcium carbonate, magnesium carbonate, and mixtures thereof.

11. A gastroretentive tablet dosage form comprising:
    a) a tablet core comprising pyridostigmine bromide, a swellable water-soluble hydrophilic polymer, and a gas-generating agent,
    b) a coating of water-insoluble permeable elastic membrane comprising an orifice, and
    c) an immediate release layer comprising pyridostigmine bromide,
    wherein the coating surrounds the tablet core,
    wherein the immediate release layer surrounds the coating such that the coating is between the tablet core and the immediate release layer, and
        wherein the water-insoluble permeable elastic membrane comprises a plasticizer, and a copolymer of ethyl acrylate, methyl methacrylate, and trimethylammonioethyl methacrylate chloride.

12. The dosage form of claim 11, wherein the plasticizer is selected from the group consisting of triethyl citrate, triacetin, polyethylene glycol, propylene glycol, and mixtures thereof.

13. The dosage form of claim 11, wherein the plasticizer is present in an amount of from about 5% wt/wt to about 20% wt/wt, based on a total weight of the copolymer and the plasticizer.

14. The dosage form of claim 11, wherein the gas generating agent is present in an amount of from about 10% wt/wt to about 25% wt/wt, based on a total weight of the tablet core.

15. The dosage form of claim 11, wherein the tablet core further comprises an acid selected from the group consisting of, succinic acid, citric acid, acetic acid, malic acid, fumaric acid, stearic acid, tartaric acid, boric acid, benzoic acid, and mixtures thereof.

16. The dosage form of claim 11, wherein the dosage form provides extended release of pyridostigmine bromide for at least about 12 hours in 900 ml of 50 mM pH 4.5 acetate buffer, measured using USP Apparatus I (custom basket) at 100 rpm.

17. The dosage form of claim 11, wherein the swellable water-soluble hydrophilic polymer in the tablet core is selected from the group consisting of hypromellose, hydroxyethyl cellulose, hydroxypropyl cellulose, carboxymethyl cellulose, microcrystalline cellulose, a polyethylene oxide polymer, and sodium alginate.

18. The dosage form of claim 11, wherein the gas-generating agent is selected from the group consisting of sodium bicarbonate, sodium carbonate, calcium carbonate, magnesium carbonate, and mixtures thereof.

19. A method for improving bioavailability of drugs with narrow absorption window in the proximal gastrointestinal (GI) tract comprising administering a gastroretentive tablet dosage form comprising:
    a) a tablet core comprising a drug with narrow absorption window in the upper GI trat tract, a swellable water-soluble hydrophilic polymer, and a gas-generating agent, and
    b) a coating of water-insoluble permeable elastic membrane comprising an orifice,
    wherein the coating surrounds the tablet core, and
    wherein the water-insoluble permeable elastic membrane comprises a plasticizer, and a copolymer of ethyl acrylate, methyl methacrylate, and trimethylammonioethyl methacrylate chloride.

20. The method of claim 19, wherein the dosage form further comprises an immediate release layer comprising a second drug with narrow absorption window in the upper GI tract, wherein the second drug in the immediate release layer is same as the drug in the tablet core.

* * * * *